(12) United States Patent
Grant et al.

(10) Patent No.: US 8,672,879 B2
(45) Date of Patent: Mar. 18, 2014

(54) DEVICES, SYSTEMS AND RELATED METHODS SUITABLE FOR DELIVERY OF A LIQUID MEDICAMENT STORED AT CRYOGENIC TEMPERATURES

(75) Inventors: Richard Grant, St Kilda West (AU); Christopher John Leigh-Lancaster, Murrumbeena (AU); Andrew Zipsin, Briar Hill (AU); Timothy Peele, Raleigh, NC (US); Ian S. Fitzpatrick, Mt. Eliza (AU)

(73) Assignee: Argos Therapeutics, Inc., Durham, NC (US)

( * ) Notice: Subject to any disclaimer, the term of this patent is extended or adjusted under 35 U.S.C. 154(b) by 568 days.

(21) Appl. No.: 12/066,865

(22) PCT Filed: Oct. 13, 2006

(86) PCT No.: PCT/US2006/040491
§ 371 (c)(1),
(2), (4) Date: Sep. 8, 2008

(87) PCT Pub. No.: WO2007/044980
PCT Pub. Date: Apr. 19, 2007

(65) Prior Publication Data
US 2009/0204071 A1 Aug. 13, 2009

Related U.S. Application Data

(60) Provisional application No. 60/726,396, filed on Oct. 13, 2005.

(51) Int. Cl.
*A61M 31/00* (2006.01)
*A61F 7/12* (2006.01)
*A61M 1/00* (2006.01)
*A61M 5/00* (2006.01)
*A61M 5/24* (2006.01)
*A61M 5/28* (2006.01)

(52) U.S. Cl.
USPC .......... 604/93.01; 604/48; 604/506; 604/113; 604/153; 604/181; 604/200

(58) Field of Classification Search
USPC ................. 604/113, 232, 291, 151–155, 905, 604/518–520, 522, 411–414, 82–86, 891.1; 220/284, 277, 265, 260; 215/302, 297, 215/296, 295; D9/437, 436, 435
See application file for complete search history.

(56) References Cited

U.S. PATENT DOCUMENTS 2,727,516 A * 12/1955 Lockhart ...................... 600/578
2,907,328 A * 10/1959 Cohen .......................... 604/113
(Continued)

FOREIGN PATENT DOCUMENTS

JP 49-94487 7/1974
JP 54-165258 11/1979
(Continued)

OTHER PUBLICATIONS

International Search Report and Written Opinion of the International Searching Authority, issued in reference to International Application No. PCT/US06/40491, Mail date: Jul. 1, 2008.

(Continued)

*Primary Examiner* — Nicholas Lucchesi
*Assistant Examiner* — Jenna Zhang
(74) *Attorney, Agent, or Firm* — Myers Bigel Sibley & Sajovec, P.A.

(57) ABSTRACT

Medicament devices include a sealed medicament dose container comprising a cell based medicament that is stored at a temperature less than about −40 degrees Celsius, then thawed into a liquid prior to administration and a medicament dose cartridge configured and sized to snugly hold the dose container therein during extraction of the liquid medicament. Related dose containers, retainers and extraction/dispensing systems are also described.

62 Claims, 21 Drawing Sheets

(56) References Cited

U.S. PATENT DOCUMENTS

| | | | | |
|---|---|---|---|---|
| 3,938,513 | A | * | 2/1976 | Hargest .................. 604/190 |
| 3,946,732 | A | * | 3/1976 | Hurscham .................. 604/88 |
| 4,018,222 | A | * | 4/1977 | McAleer et al. ............ 604/113 |
| 4,070,453 | A | * | 1/1978 | Bordt et al. .................. 435/325 |
| 4,331,265 | A | * | 5/1982 | Warlick ...................... 222/101 |
| 4,632,673 | A | * | 12/1986 | Tiitola et al. ............... 604/415 |
| 4,664,659 | A | * | 5/1987 | Shinohara ................... 604/533 |
| 4,821,907 | A | * | 4/1989 | Castles et al. ................ 62/430 |
| 5,330,431 | A | * | 7/1994 | Herskowitz .................. 604/153 |
| 5,346,481 | A | * | 9/1994 | Bunin ........................... 604/204 |
| 5,354,286 | A | * | 10/1994 | Mesa et al. .................. 604/230 |
| 5,626,566 | A | | 5/1997 | Petersen et al. ............... 604/208 |
| 5,695,477 | A | * | 12/1997 | Sfikas ............................ 604/241 |
| 5,750,101 | A | * | 5/1998 | Stone ........................... 424/85.2 |
| 5,846,225 | A | | 12/1998 | Rosengart et al. | |
| 5,846,233 | A | | 12/1998 | Lilley et al. | |
| 5,868,710 | A | * | 2/1999 | Battiato et al. ................ 604/123 |
| 5,924,852 | A | | 7/1999 | Moubayed et al. ............ 417/474 |
| 5,980,490 | A | | 11/1999 | Tsoukalis ...................... 604/151 |
| 6,036,675 | A | * | 3/2000 | Thorne et al. ................ 604/232 |
| 6,045,538 | A | | 4/2000 | Farris ............................ 604/243 |
| 6,120,478 | A | | 9/2000 | Moore et al. | |
| 6,355,023 | B1 | | 3/2002 | Roth et al. .................... 604/411 |
| 6,547,099 | B1 | * | 4/2003 | Farris ............................ 222/95 |
| 6,585,698 | B1 | * | 7/2003 | Packman et al. .............. 604/207 |
| 6,605,066 | B1 | * | 8/2003 | Gravagna et al. ............. 604/191 |
| 6,622,731 | B2 | * | 9/2003 | Daniel et al. .................. 128/898 |
| 6,644,509 | B1 | * | 11/2003 | Bublewitz et al. ............ 222/88 |
| 6,746,438 | B1 | | 6/2004 | Arnissolle ..................... 604/411 |
| 6,918,418 | B1 | | 7/2005 | Farris ............................ 141/319 |
| 2003/0045499 | A1 | * | 3/2003 | Gabrilovich et al. .......... 514/44 |
| 2006/0178620 | A1 | * | 8/2006 | Wollmann et al. ............ 604/88 |

FOREIGN PATENT DOCUMENTS

| | | |
|---|---|---|
| JP | 07067937 | 3/1995 |
| JP | 08257101 | 10/1996 |
| JP | 2003116964 | 4/2003 |

OTHER PUBLICATIONS

International Preliminary Report on Patentability for PCT application No. PCT/US06/40491, date of mailing Mar. 8, 2011.

* cited by examiner

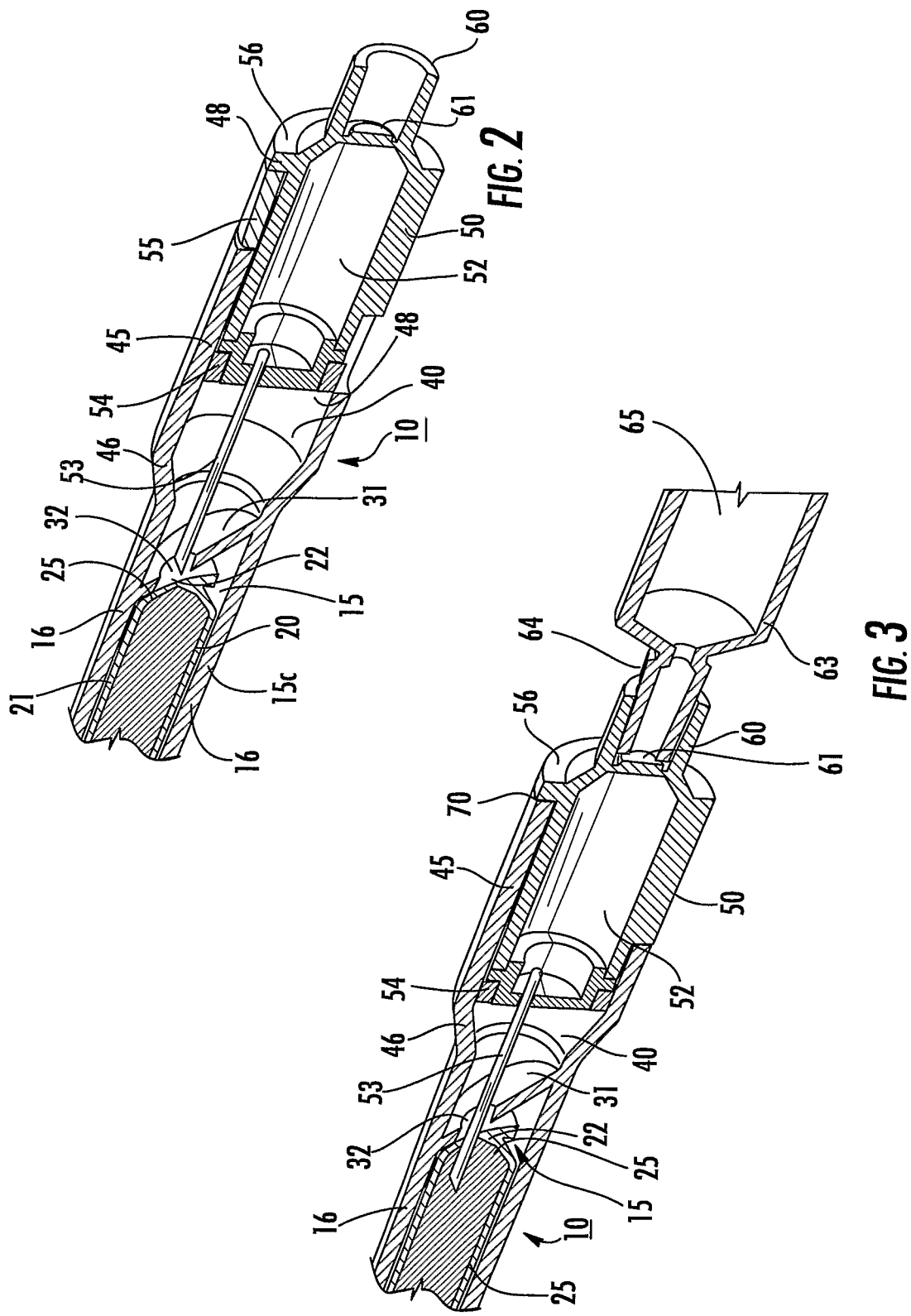

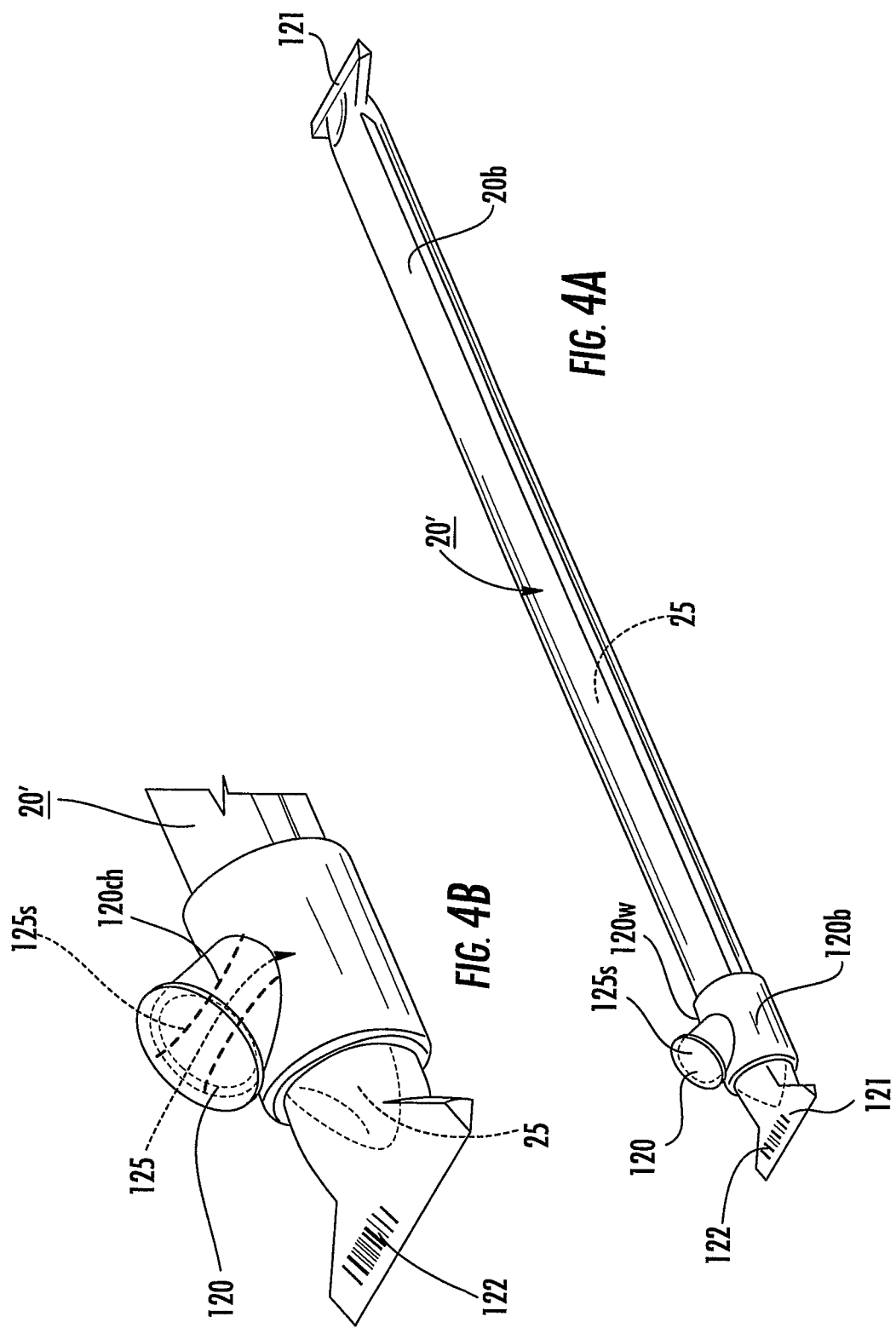

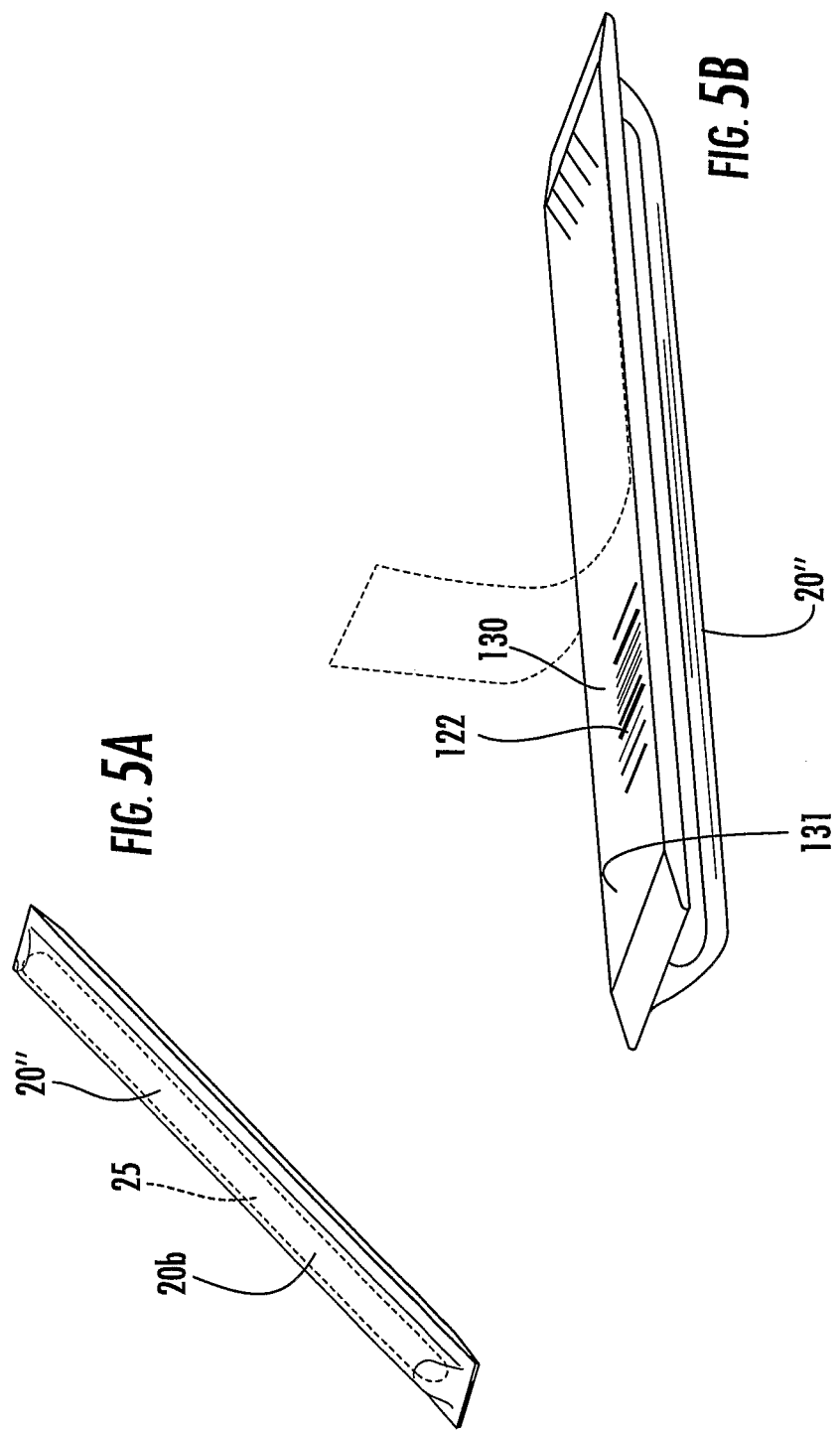

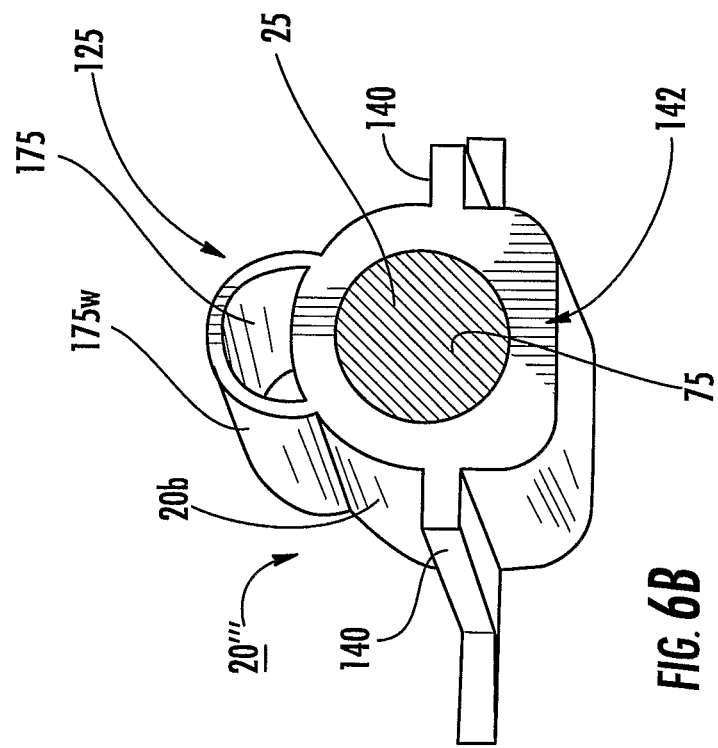
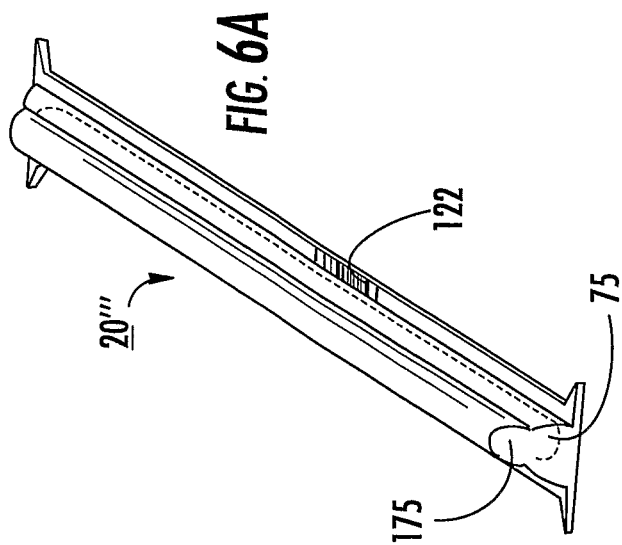

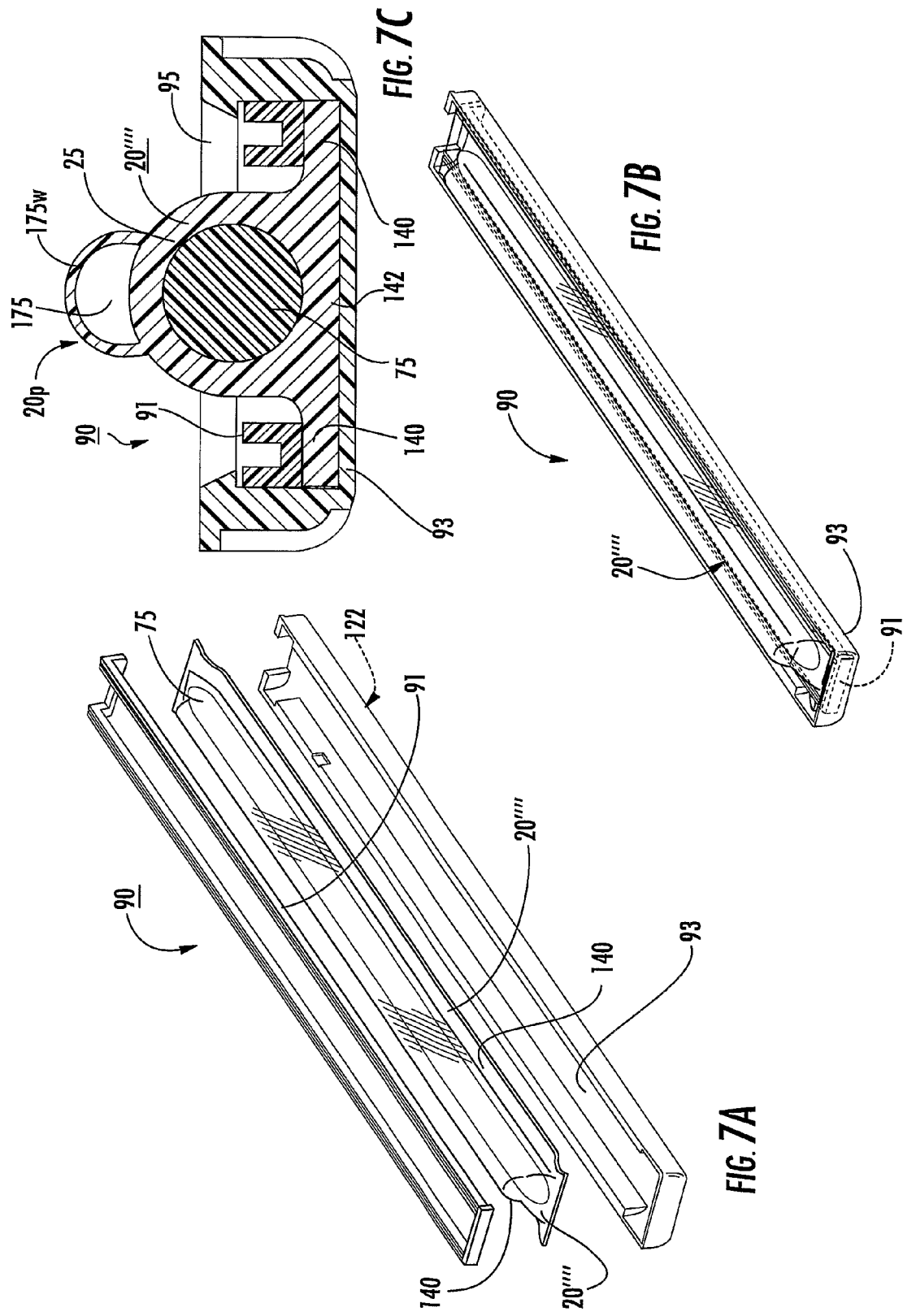

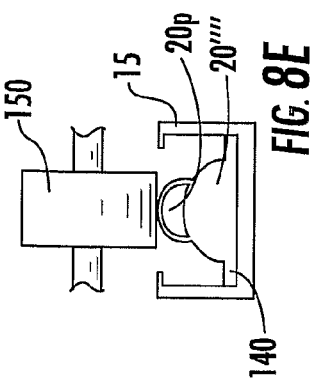
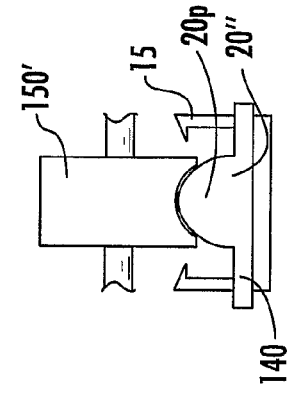
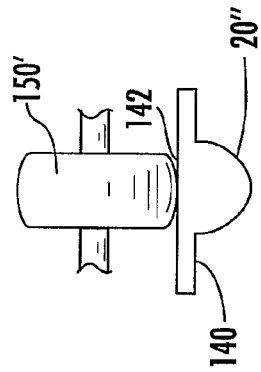
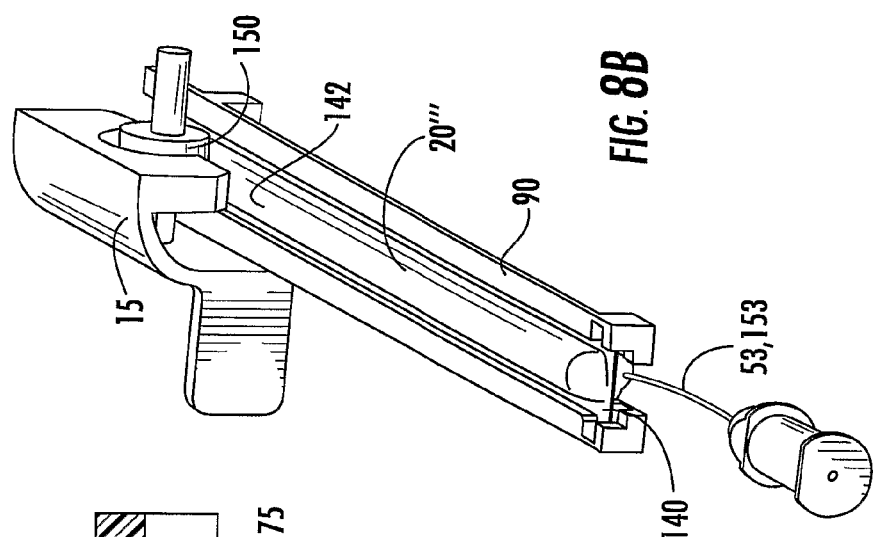
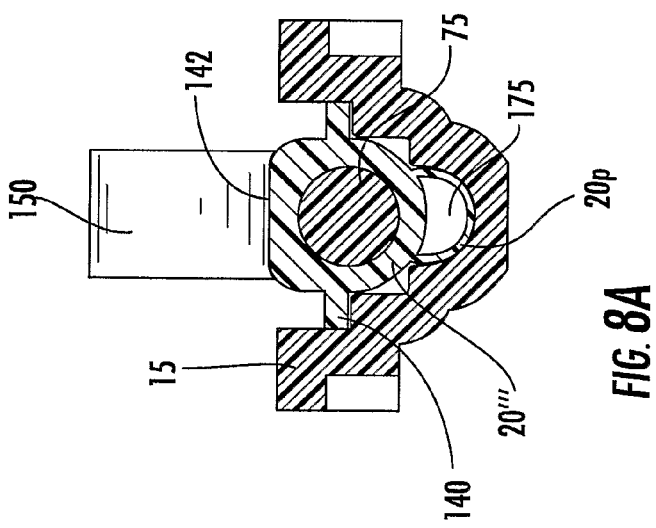

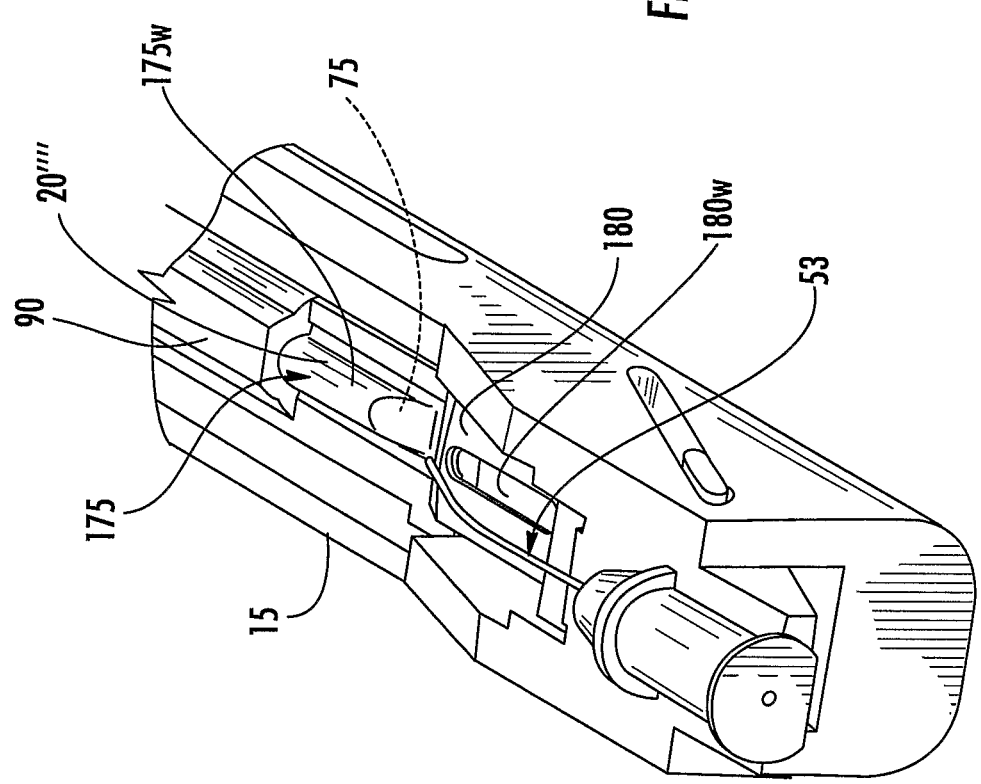
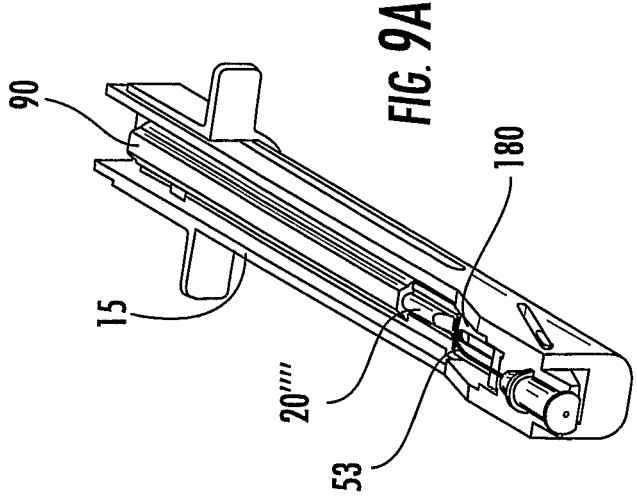
FIG. 9B
FIG. 9A

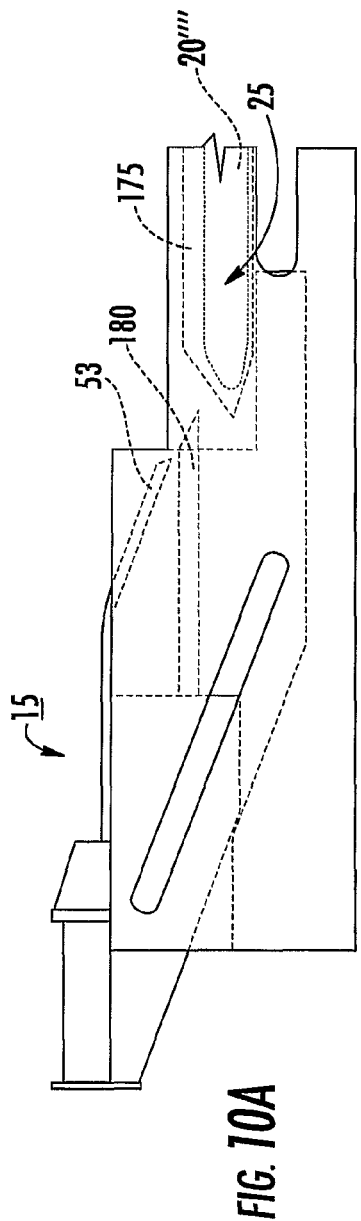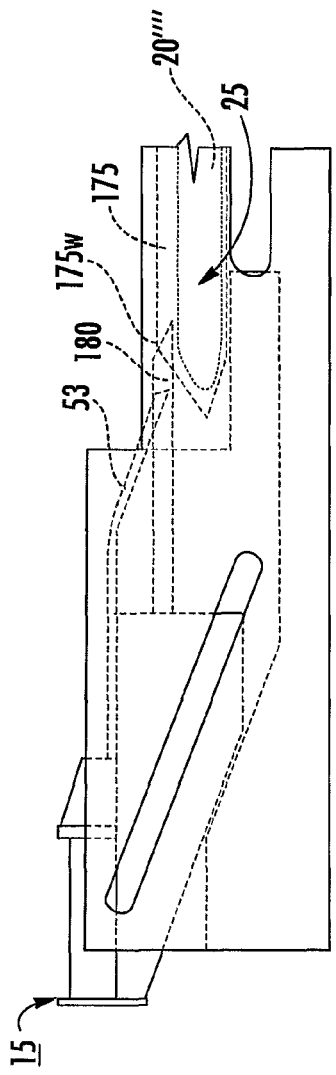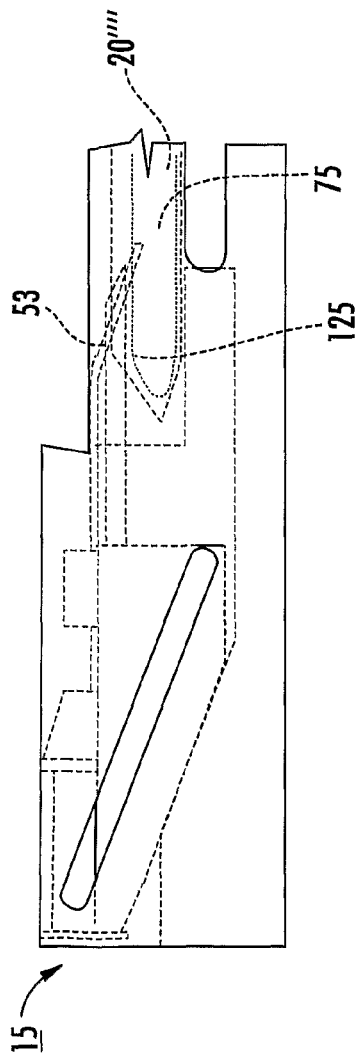

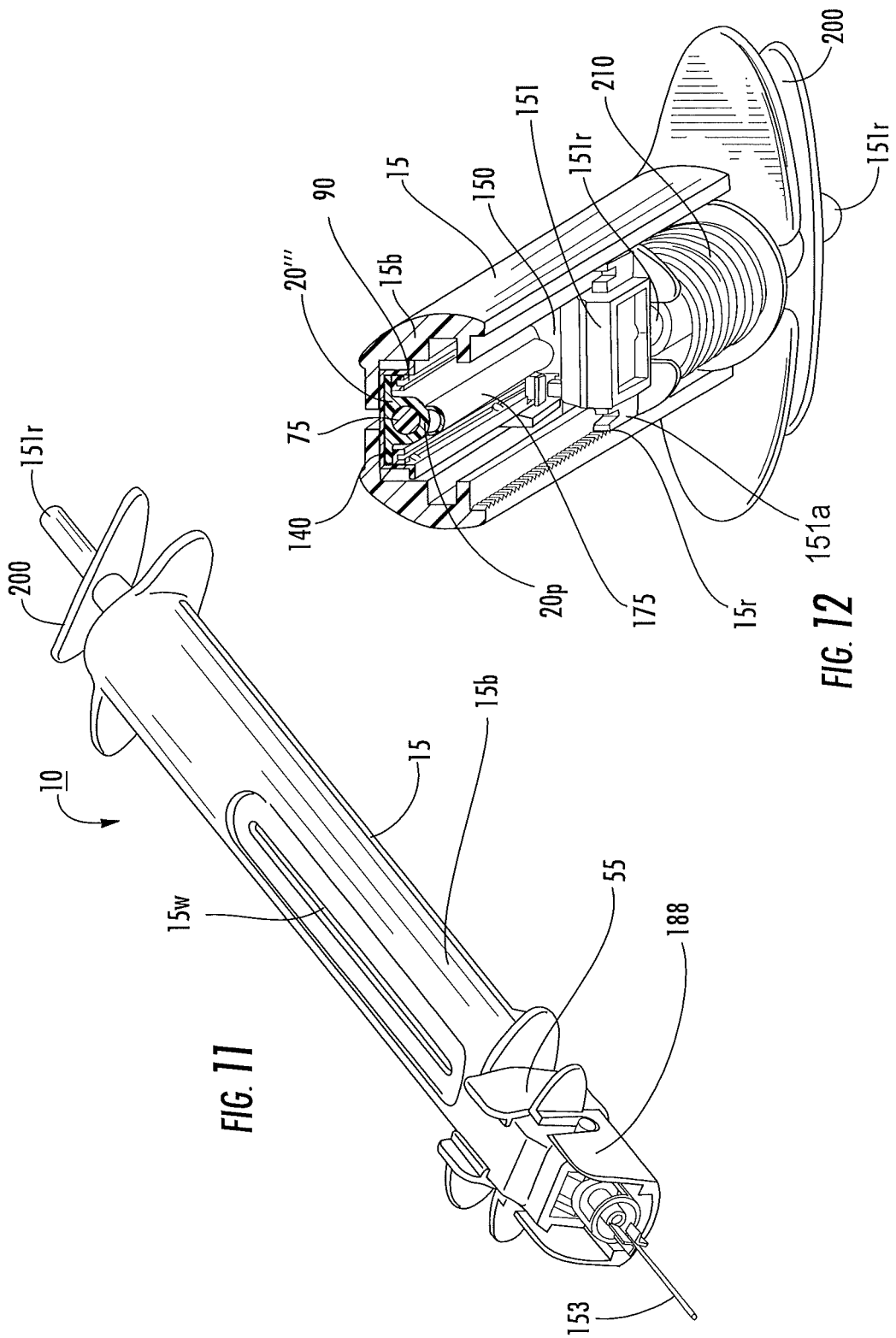

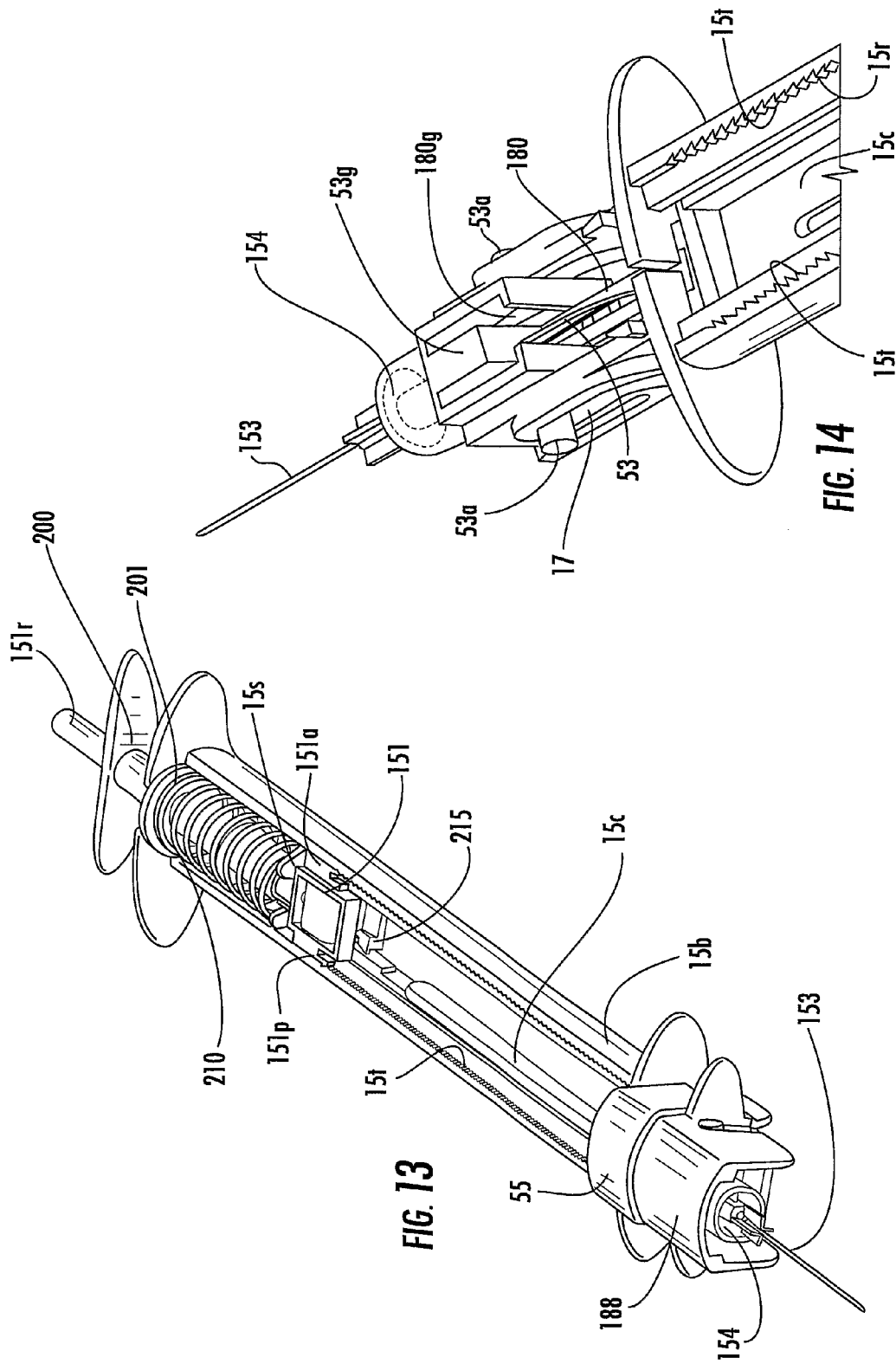

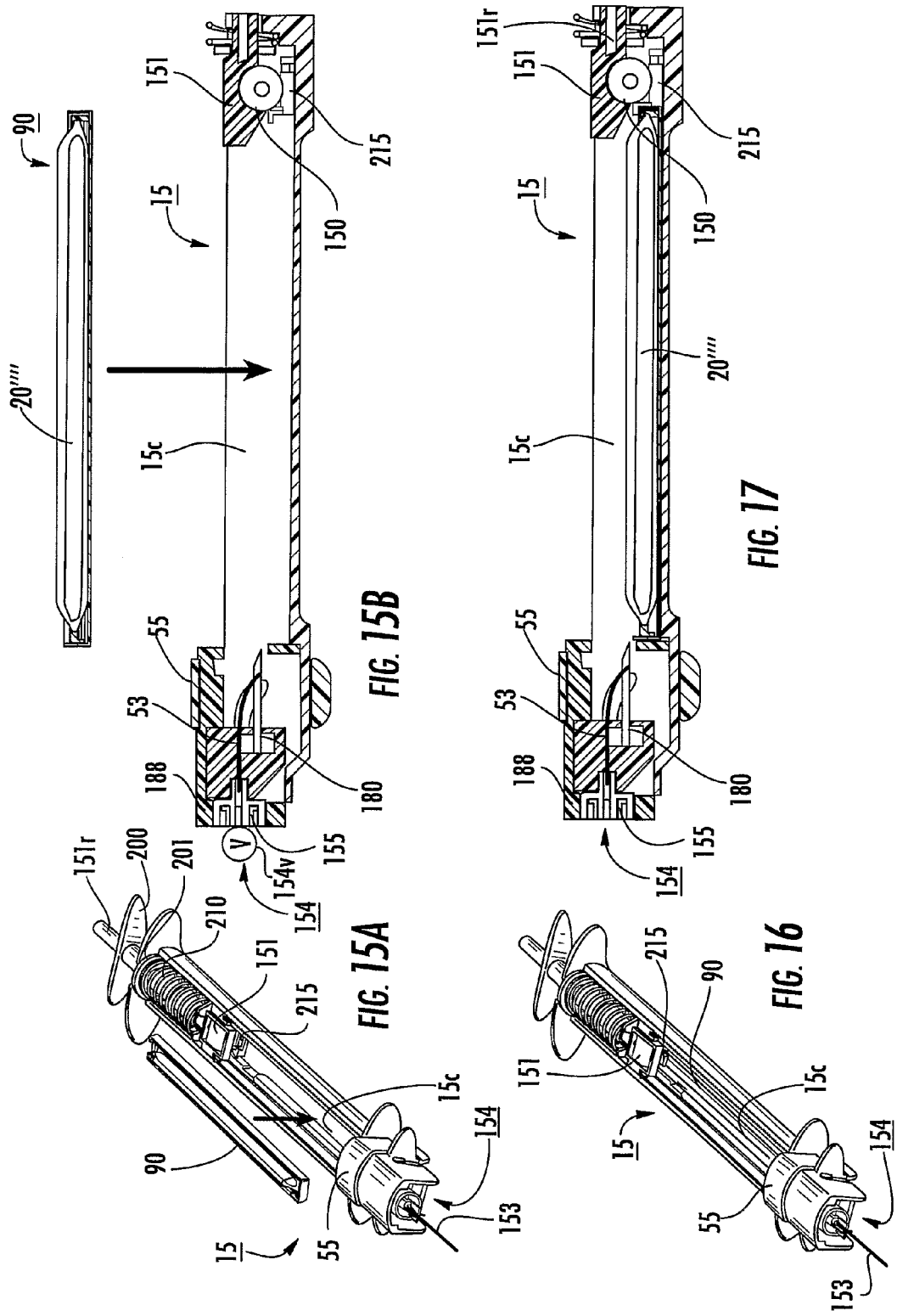

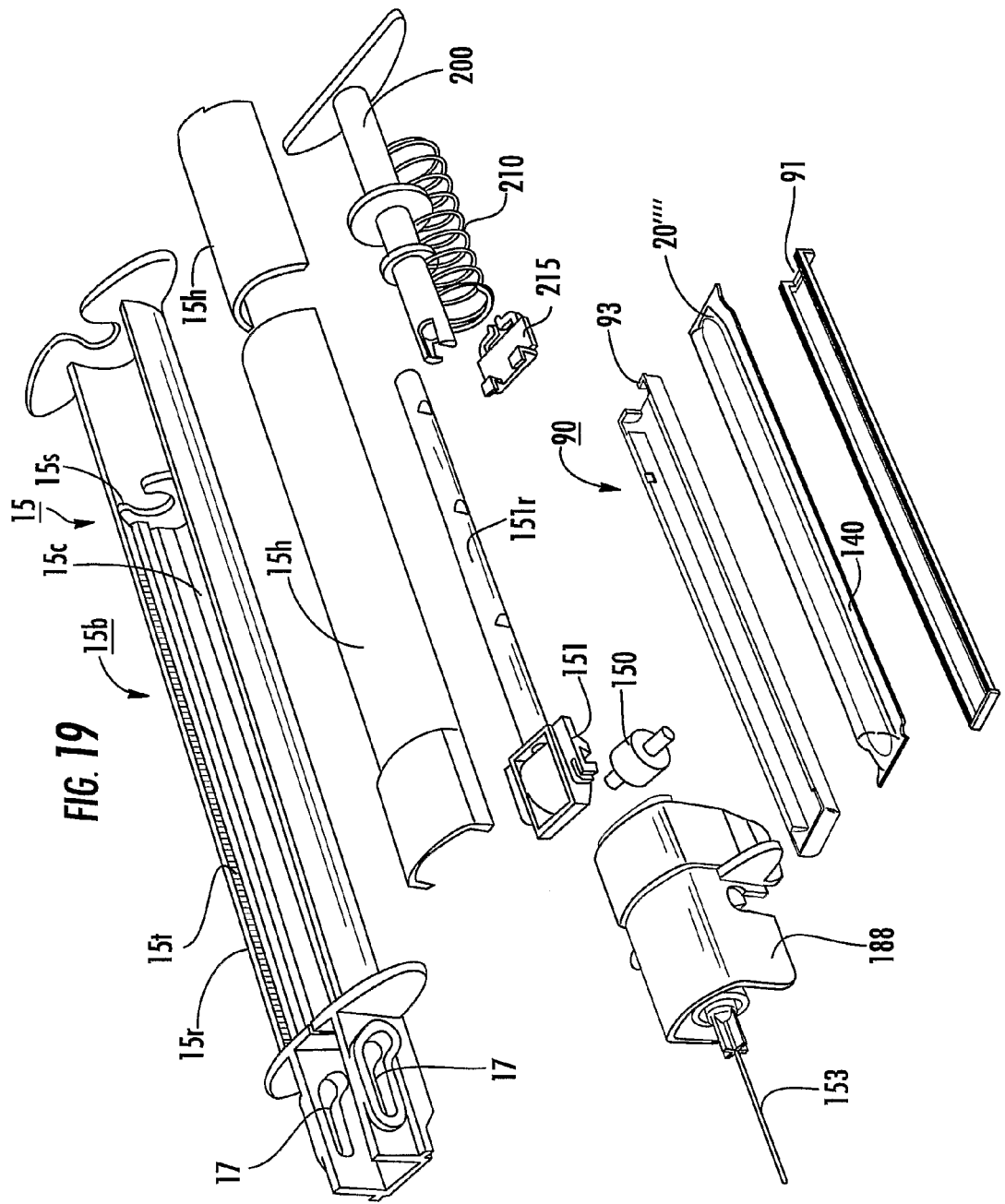

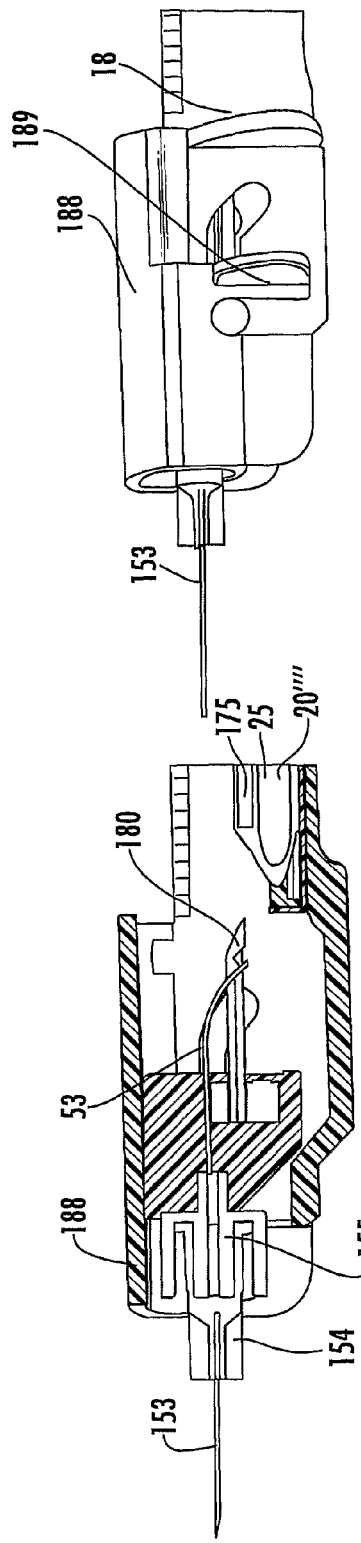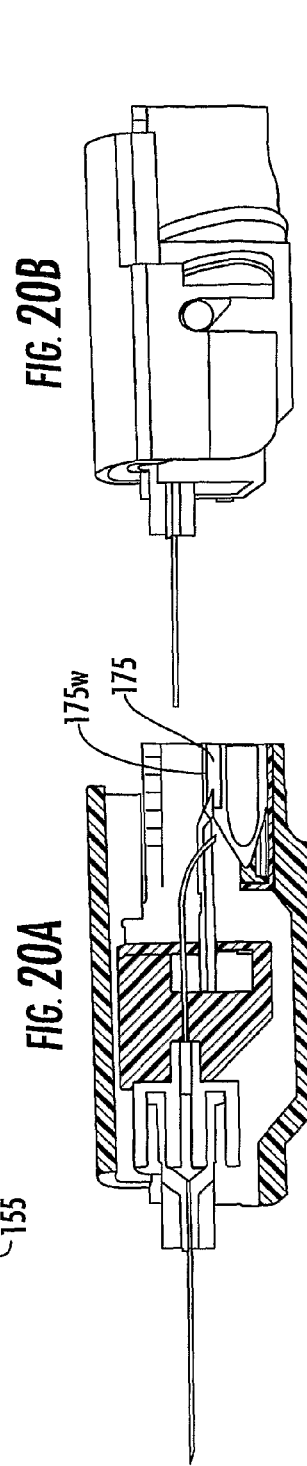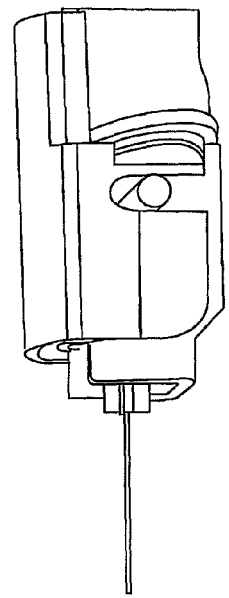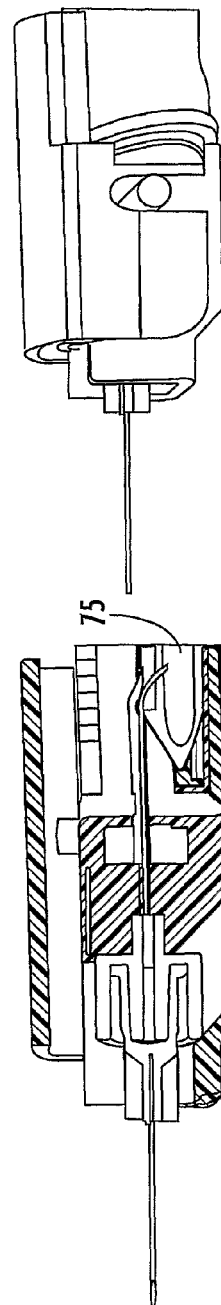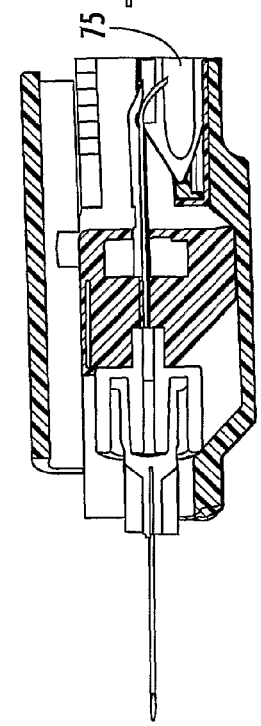

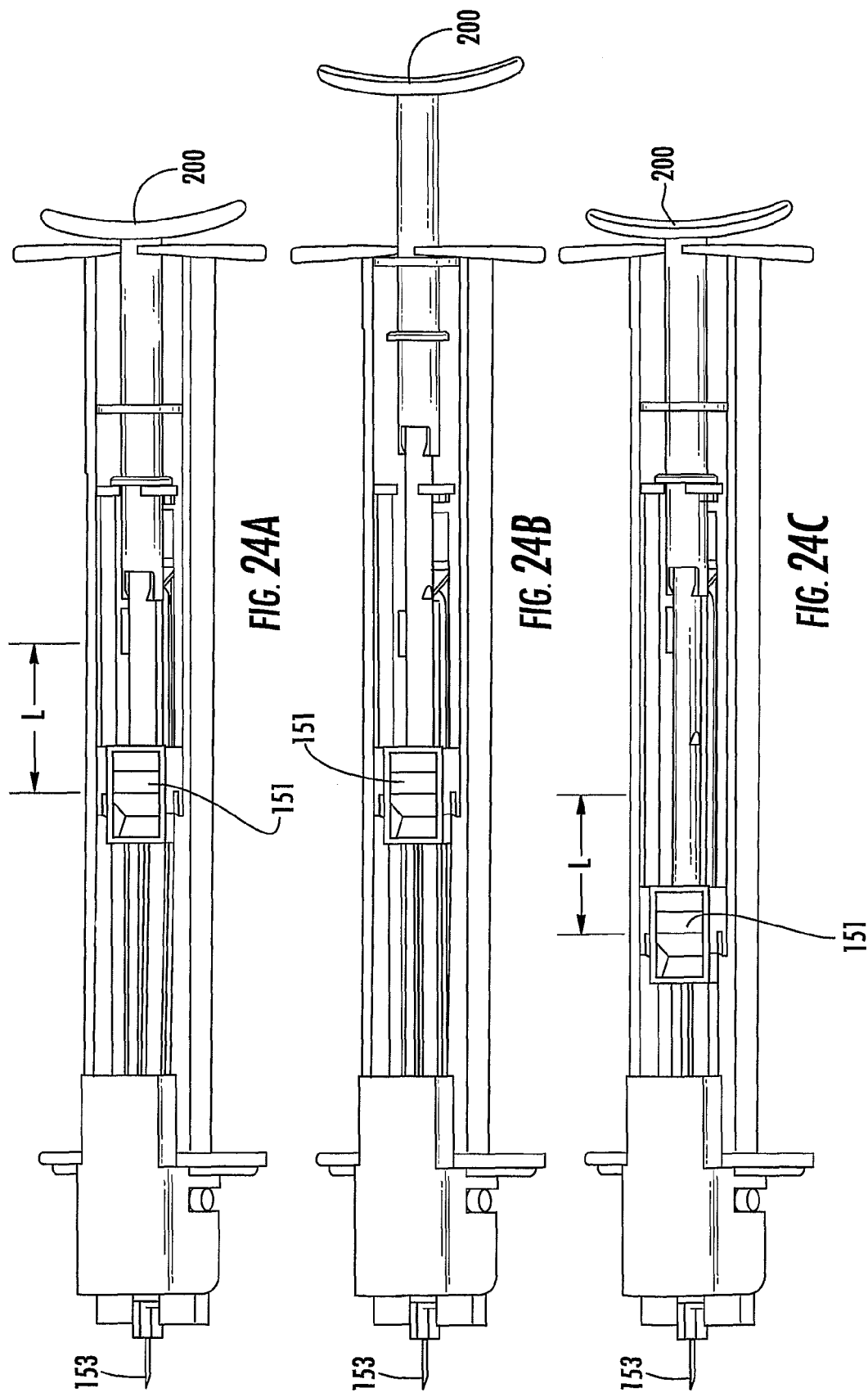

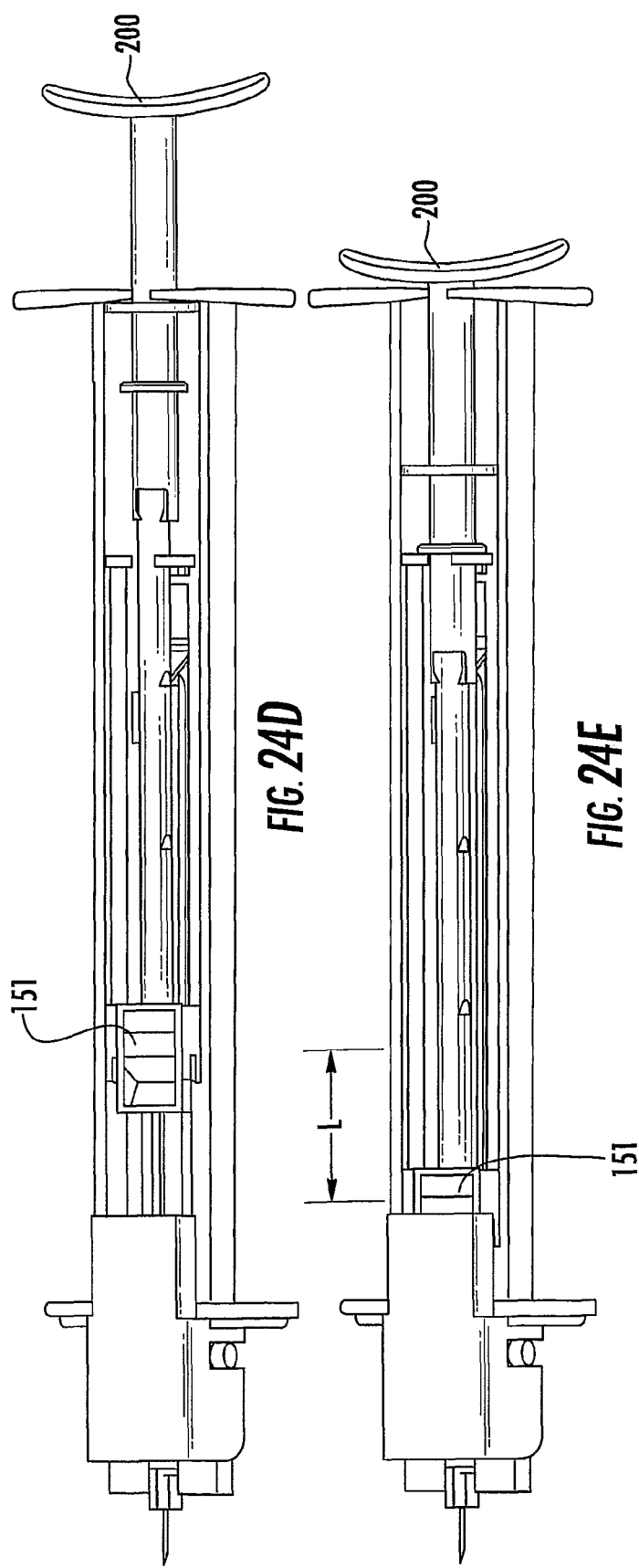

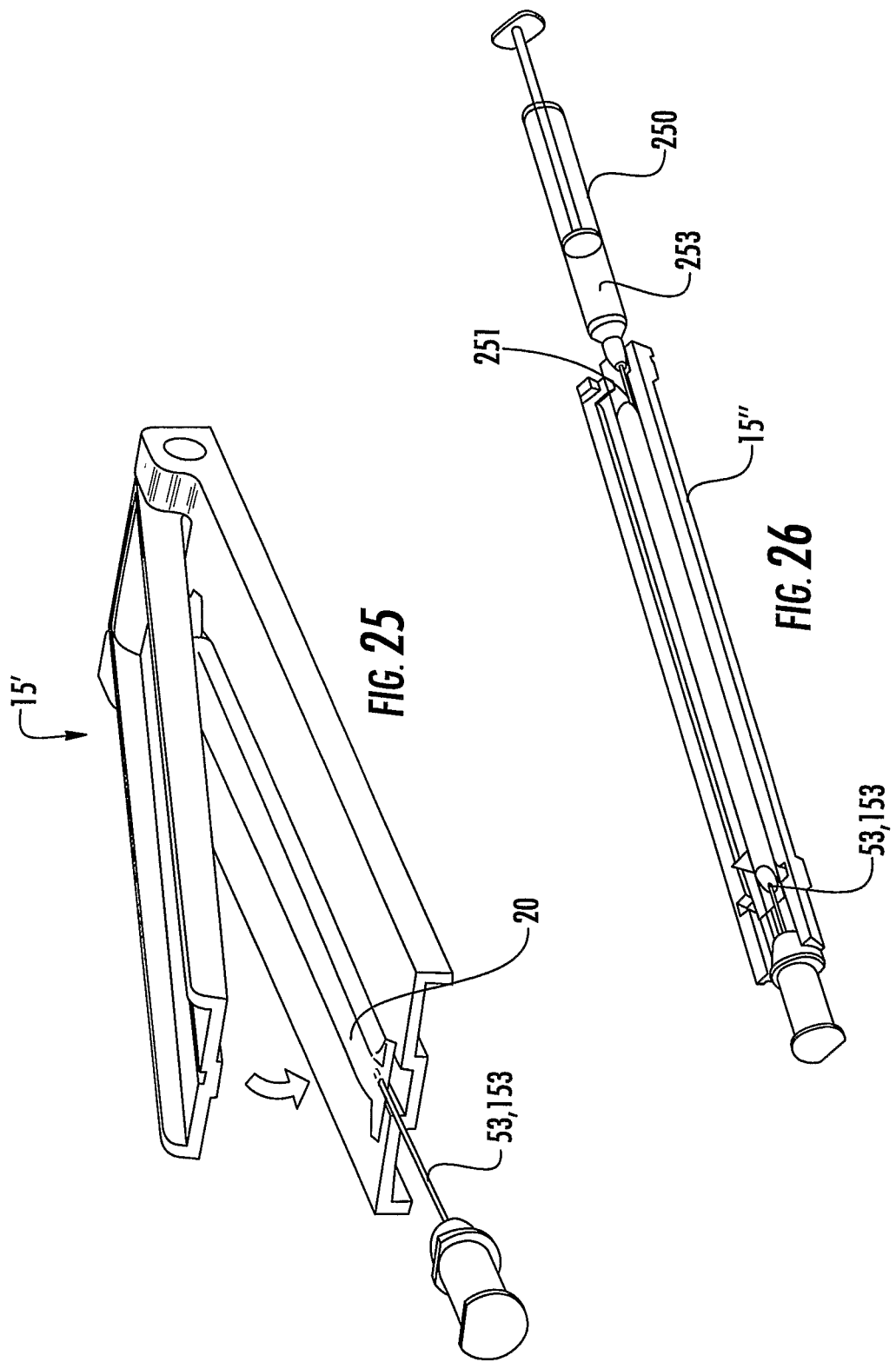

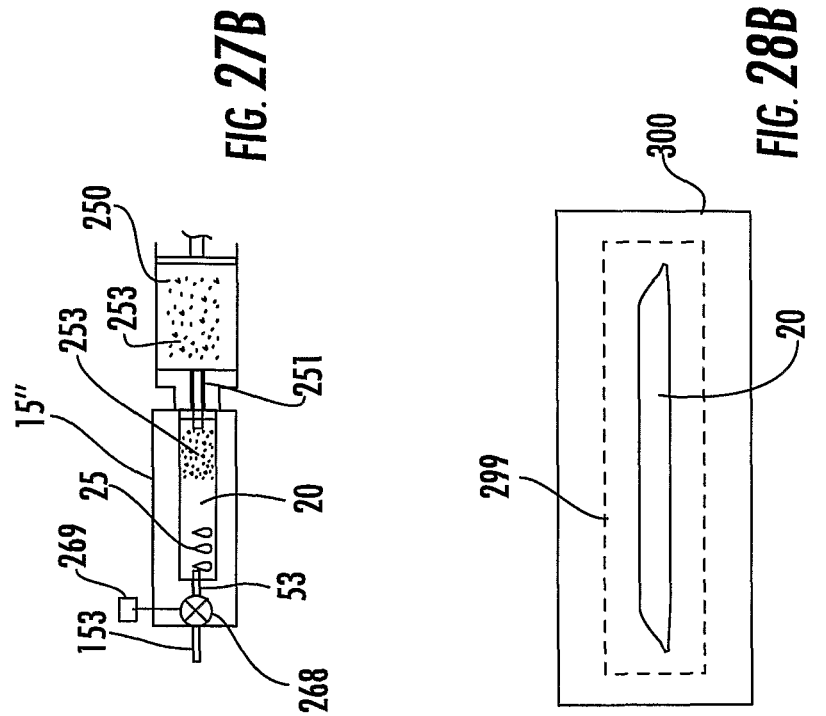
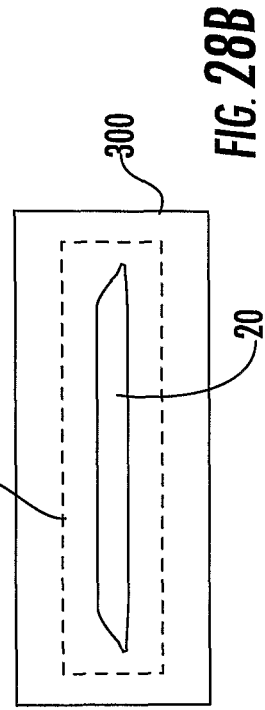
FIG. 27A
FIG. 27B
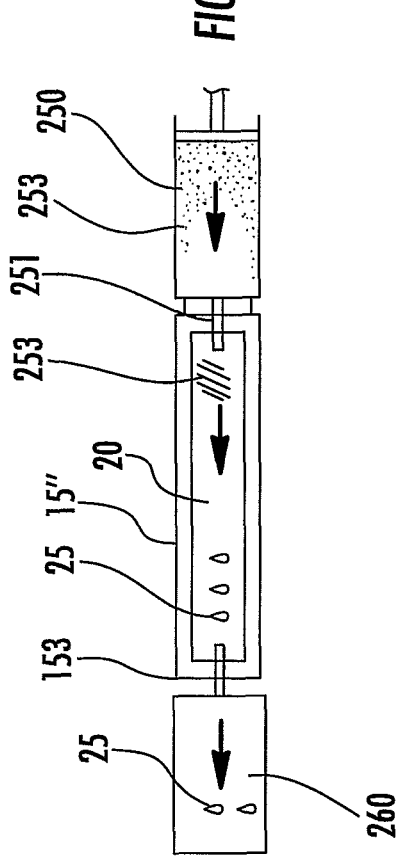
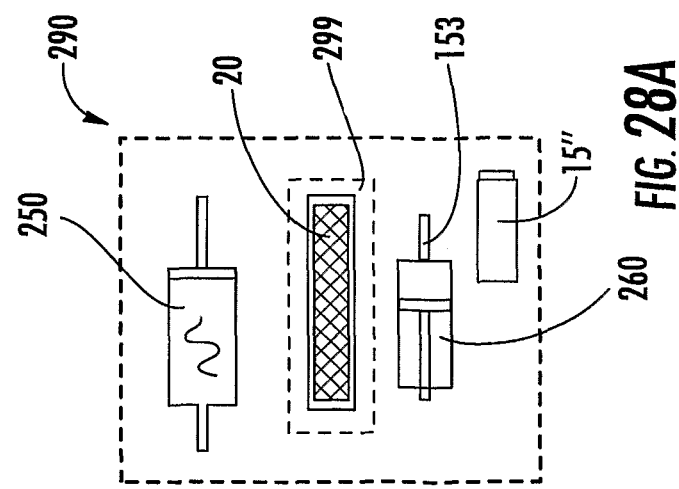
FIG. 28A
FIG. 28B

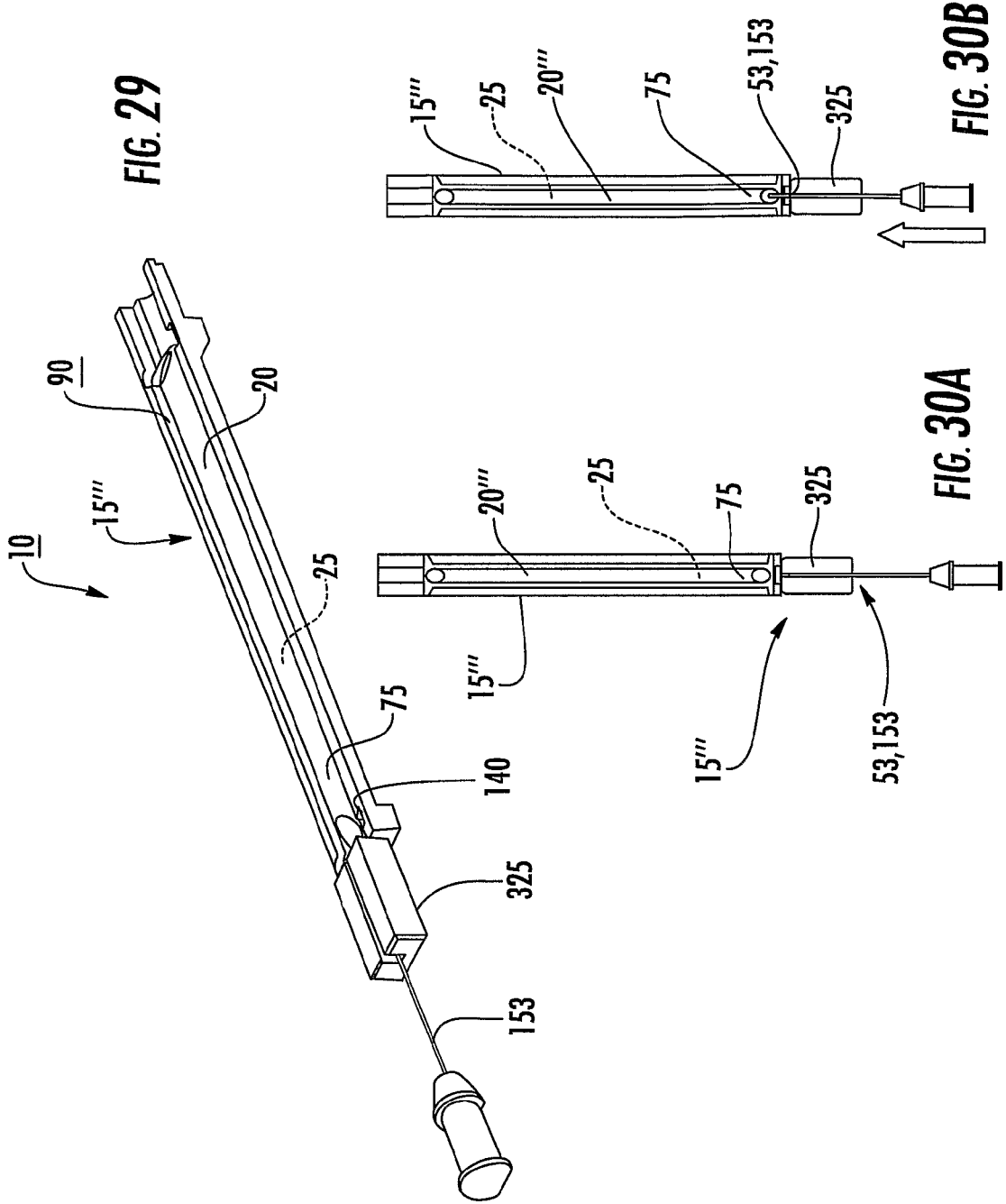

DEVICES, SYSTEMS AND RELATED METHODS SUITABLE FOR DELIVERY OF A LIQUID MEDICAMENT STORED AT CRYOGENIC TEMPERATURES

RELATED APPLICATIONS

This application is a 35 USC 371 national phase application of PCT/US2006/040491, filed Oct. 13, 2006, which claims the benefit of U.S. Provisional Patent Application Ser. No. 60/726,396, filed Oct. 13, 2005, the contents of which are hereby incorporated by reference as if recited in full herein.

FIELD OF THE INVENTION

This invention relates to the delivery and/or transfer of fluid medicaments, especially vaccines, and may be particularly suitable for the delivery and/or transfer of fluid medicaments that are stored and held at ultra-low and/or cryogenic temperatures prior to administration.

BACKGROUND OF THE INVENTION

In general, vaccines can be harvested, then, after suitable treatment, can be lyophilized and kept at low temperatures, typically around 0 degrees Celsius (° C.), for extended periods of time prior to use. While lyophilization may be a suitable approach to preservation of some substances, some vaccines and other medicaments do not readily lyophilize and, in addition, dilution of a lyophilized product can be difficult to accomplish, especially in a sterile environment, by the end user.

Some vaccines and other liquid medicaments may need to be kept at even colder temperatures in order to give the vaccine a commercially reasonable shelf life and/or to promote viability or efficacy of the medicament.

For example, during clinical trials by Argos Therapeutics, Inc., plastic tubes with removable lids have been used to cryogenically store custom-prepared liquid vaccines derived from a patient's own cells, in a frozen state, at less than about −40° C. Prior to administration, the medicament was thawed to liquid in the tube and the lid removed. Three syringes were used to extract the liquid medicament from the opened tube while the lid remained off the tube, then each syringe of liquid medicament was injected into the patient within a relatively short period of time after thaw to deliver the desired bolus dose.

Despite the above, there is a need to provide containers and/or cooperating delivery systems that are economic, reliable in dispensing volume, relatively easy to manufacture and able to withstand ultra-low and/or cryogenic temperatures, such as about or below −40° C., about or below −70° C., or even about or below −80° C., such as between about −120° C. to about −196° C. There is also a need for such devices to meet cleanliness and/or sterility standards in commercial production systems while protecting the medicaments from environmental exposure prior to and/or during administration.

SUMMARY OF EMBODIMENTS OF THE INVENTION

Embodiments of the invention provide delivery devices that can be used to deliver medicaments to a patient, directly or indirectly.

Some embodiments of the invention are directed to medicament holding devices. The devices include: (a) a sealed medicament dose container comprising a medicament that is stored frozen (and may be cryogenically stored at a temperature that is less than about −40° C. for at least some portion of the storage cycle) then thawed into a liquid prior to administration; and (b) a medicament dose cartridge configured and sized to snugly hold the dose container therein during extraction of the liquid medicament.

The sealed dose container with medicament may be stored for at least some portion of its life at a temperature that is about −70° C. or less, such as for example, between about −70° C. to about −196° C. In some embodiments, the medicament can be held between about −120° C. to about −196° C. for at least a portion of its life before use.

In particular embodiments, the dose cartridge has a body with greater rigidity than that of the dose container, and is configured to substantially enclose the dose container therein. The device can define a unitary assembly that is a unit dose single-use disposable device.

In some embodiments, the dose cartridge can include a first end portion having an internal needle configured to translate from a non-use retracted position to an extraction position whereby the needle pierces the dose container and is in fluid communication with the liquid medicament during extraction of the medicament.

In some embodiments, the dose cartridge can include an external safety stop or locking member in communication with the needle to prevent inadvertent piercing of the dose container.

Other embodiments are directed to dose medicament transfer and/or delivery devices that include: (a) a dose container comprising a medicament, wherein the dose container with medicament are adapted to be stored at a temperature sufficient to freeze the liquid medicament in the container, and wherein the medicament is configured to be in liquid form proximate in time to delivery to a patient; (b) a cartridge configured to hold the dose container therein; and (c) a liquid medicament expulsion system in the cartridge configured to serially expel fixed volumes of liquid medicament from the dose container.

In particular embodiments, the expulsion system includes a pressing mechanism configured to serially axially compress portions of the dose container from a top portion to a bottom portion thereof. The pressing mechanism may include a roller with a roller guide that is configured to axially travel from a first end portion of the cartridge toward a second end portion of the cartridge.

Other embodiments are directed to kits for delivering a liquid medicament. The kits include: (a) a syringe of sterile gas; (b) a dose container comprising liquid medicament; and (c) a cartridge sized and configured to snugly hold the dose container therein. In use, the syringe of sterile gas is configured to cooperate with the dose cartridge to expel the liquid medicament from the dose container.

Some embodiments are directed to methods of expelling a liquid medicament from a dose container. The methods include: (a) providing a cartridge holding a dose container of liquid medicament therein; (b) attaching a first syringe comprising sterile fluid therein to the cartridge; (c) introducing the sterile fluid from the syringe into a first end portion of the dose container; then (d) pushing the liquid medicament out of a second end portion of the dose container in response to the introducing step.

Still other embodiments are directed to methods of delivering a liquid medicament, that include: (a) providing a container holding a liquid medicament in a frozen state; (b) thawing the liquid medicament at a therapy administration site; (c) heating a needle at the administration site; (d) using the needle after the heating step to pierce the container at the administration site; then (e) injecting the liquid medicament into the subject.

In some particular embodiments, the injecting can be carried out within about 1 hour of the thawing step.

Still other embodiments are directed to methods of obtaining liquid medicament from a sealed container that has been stored in a frozen state. The methods include: (a) thawing a container holding a liquid medicament proximate in time to administration of the medicament to a patient; (b) inserting the container in a cartridge having a needle with a lumen therein; (c) advancing the needle or the cartridge so that the needle pierces the container in the cartridge; then (d) directing at least a portion of the liquid medicament to exit the container through the needle.

Some embodiments are directed to methods of transferring and/or delivering liquid medicaments. The methods include: (a) cryogenically storing a container with a frozen liquid medicament therein; (b) thawing the frozen liquid medicament at a dispensing site; (c) serially activating or operating a dispensing system associated with a cartridge holding the container with the liquid medicament to direct the liquid medicament to exit the container in a plurality of fixed volume amounts.

The serially activating or operating step may include moving a roller unidirectionally axially while pressing against the dose container, the roller having a plurality of serial forward stroke lengths that define the exiting fixed volume amounts.

Still other embodiments are directed to sealed sterile elongate medicament containers (that may be extruded) comprising a pharmaceutical medicament adapted to be frozen then thawed into liquid in the container prior to administration.

The container may have cross-sectional profile shape with a substantially concave portion merging into a substantially planar portion and/or may include first and second outwardly extending substantially planar wings.

The instant invention provides devices for delivery and/or transfer of a fluid medicament via direct injection into a patient or via indirect delivery, using, for example, a syringe for administration to a patient.

Other systems and/or methods according to embodiments of the invention will be or become apparent to one with skill in the art upon review of the following drawings and detailed description. It is intended that all such additional systems, methods, and/or devices be included within this description, be within the scope of the present invention, and be protected by the accompanying claims.

BRIEF DESCRIPTION OF THE DRAWINGS

Other features of the present invention will be more readily understood from the following detailed description of exemplary embodiments thereof when read in conjunction with the accompanying drawings.

FIG. 2 is a perspective section view of the device shown in FIG. 1.

FIG. 3 is a perspective section view of the device shown in FIG. 1, illustrating the plunger engaged and a syringe in place to receive the medicament, according to embodiments of the present invention.

FIG. 4A is a side perspective view of a dose container according to some embodiments of the present invention.

FIG. 4B is a greatly enlarged side perspective view of a portion of the dose container shown in FIG. 4A.

FIG. 5A is a top perspective view of another embodiments of a dose container according to embodiments of the present invention.

FIG. 5B is a bottom perspective view of the dose container shown in FIG. 5A.

FIG. 6A is a top perspective view of another embodiment of a dose container according to embodiments of the present invention.

FIG. 6B is a greatly enlarged section view of the dose container shown in FIG. 6A.

FIG. 7A is an exploded view of a dose retainer and dose container according to embodiments of the present invention.

FIG. 7B is a side perspective view of the assembly of the dose retainer and container shown in FIG. 7A.

FIG. 7C is a greatly enlarged section view of the assembly shown in FIG. 7B.

FIG. 8A is a greatly enlarged partial section view of a dose container held in a cartridge with a roller medicament-dispensing/extraction member according to some embodiments of the present invention.

FIG. 8B is a partial cutaway side perspective view of the assembly shown in FIG. 8A.

FIGS. 8C-8E are schematic greatly enlarged partial section views of alternative configurations of a dose container and roller medicament-dispensing/extraction member according to some embodiments of the present invention.

FIG. 9A is a top perspective partial view of a cartridge with a dose container and a cutting member according to embodiments of the present invention.

FIG. 9B is a greatly enlarged side perspective view of a portion of the device shown in FIG. 9A.

FIGS. 10A-10C are transparent side views of a dispensing/extraction end portion of a cartridge with a dose container with a cutting member illustrating a cutting sequence according to embodiments of the present invention.

FIG. 11 is a top perspective view of a cartridge according to embodiments of the present invention.

FIG. 12 is a bottom perspective view of a portion of the cartridge shown in FIG. 11 (shown without the injection/extraction end portion and with an outer portion of the cartridge body housing removed).

FIG. 13 is a top perspective view of the opposing side of the cartridge shown in FIG. 11.

FIG. 14 is a greatly enlarged view of the injection/extraction end portion of the cartridge shown in FIGS. 11 and 13.

FIG. 15A is a top perspective view of the device shown in FIGS. 11-14, illustrating an exemplary dose container insertion configuration according to embodiments of the present invention.

FIG. 15B is a side view of the dose container insertion shown in FIG. 15A (without the external needle).

FIG. 16 is a top perspective view of the device shown in FIGS. 11-14, illustrating the exemplary dose container in the cartridge in a loaded and "ready-to-dispense" configuration according to embodiments of the present invention.

FIG. 17 is a side view of the cartridge insertion shown in FIG. 16 (without the external needle).

FIG. 19 is an exploded side view of the components shown in FIG. 18.

FIGS. 20A, 21A, and 22A are side partial cutaway views of the extraction/dispensing end portion of the cartridge shown in FIGS. 11-14 illustrating the translation of an internal needle and cutting member to open the dose container according to embodiments of the present invention.

FIGS. 20B, 21B, and 22B are side views of the extraction/dispensing end portion of the cartridge corresponding to FIGS. 20A, 21A, and 22A, respectively.

FIGS. 24A-24C are side perspective views of translation of the roller to dispense the first two doses of the liquid medicament according to some embodiments of the present invention.

FIGS. 24D and 24E are side perspective views of the translation of the roller to dispense a third dose of the liquid medicament according to some embodiments.

FIG. 25 is a side perspective view of a clamping cartridge with a dose container according to some embodiments of the present invention.

FIG. 26 is a side perspective view of a fluid extraction system with a syringe used to inject fluid according to some embodiments of the present invention.

FIG. 27A is a schematic illustration of the operation of the device shown in FIG. 26 according to some embodiments of the present invention.

FIG. 27B is a schematic illustration of a different operation of the device shown in FIG. 26 according to other embodiments of the present invention.

FIG. 28A is a schematic illustration of a kit that can be used to provide the delivery/transfer system shown in FIGS. 26 and 27.

FIG. 28B is a schematic illustration of a dose container in a cryogen bath package for shipment to a use site according to embodiments of the present invention.

FIG. 29 is a side perspective view of a needle heater unit with a cartridge according to some embodiments of the present invention.

FIGS. 30A and 30B are top views of the device shown in FIG. 29 illustrating heating a needle in situ, then using the needle to pierce the dose container according to some embodiments of the present invention.

DETAILED DESCRIPTION OF EMBODIMENTS OF THE INVENTION

Figure 1:
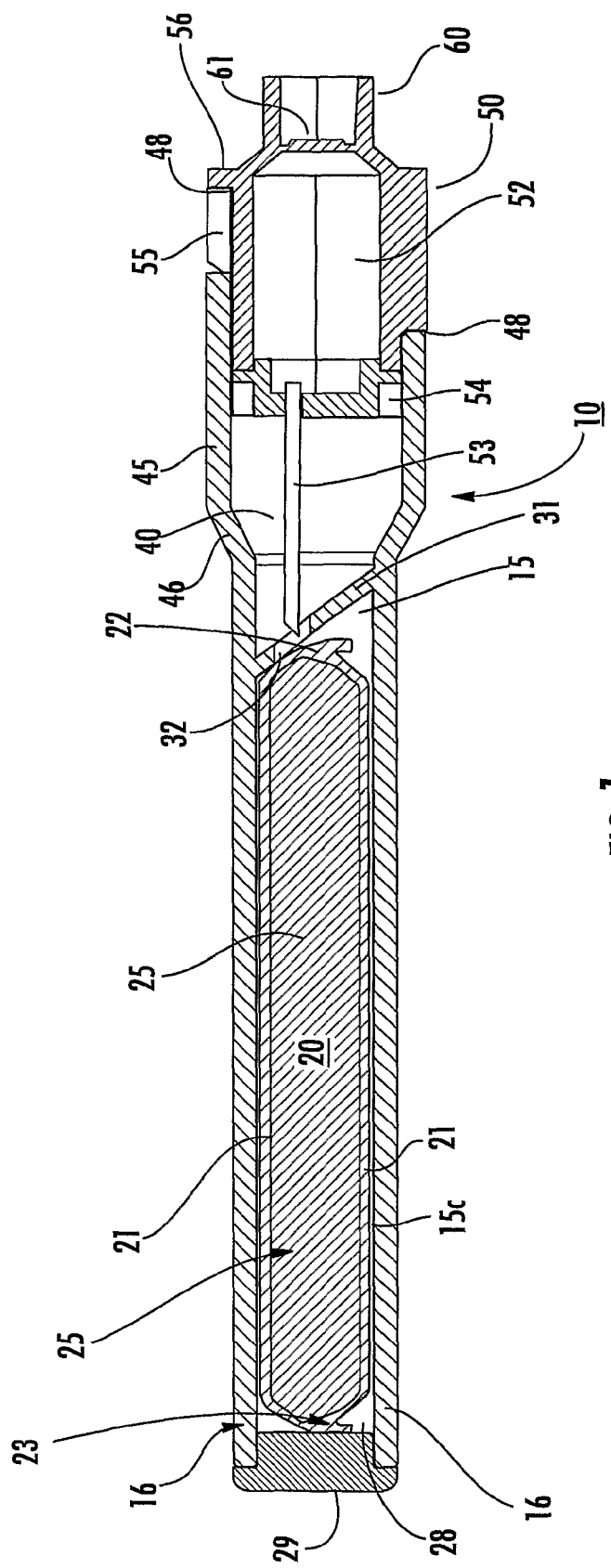
FIG. 1 is a cross section of a device of the invention according to some embodiments of the invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. One or more features shown and discussed with respect to one embodiment may be included in another embodiment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The terms "cartridge", "medicament dose cartridge", "medicament cartridge" and derivatives thereof refer to a housing body that can be used to hold a medicament dose container, which can be a multi-dose or unit dose container. The cartridge can be a sealed body or an open frame with sufficient rigidity to restrain, retain and/or hold the dose container. The cartridge can incorporate and/or cooperate with a dispensing mechanism to expel or withdraw liquid medicament. The cartridge may be used to directly inject the medicament from the dose container to a patient or to transfer the medicament to one or more syringes or other devices that are then used to deliver the medicament to the patient.

The term "sterile" refers to a surface and/or a device that is substantially free of foreign matter or undesired microorganisms. The "sterility" or "sterile" and derivatives thereof, refers to a medical grade sterility standard set, typically set by a regulatory agency. To achieve a desired sterility, the dose container or other component can be manufactured (filled and sealed) at a controlled clean-standard site, such as, for example, a "Class 100,000" site or better. The manufacturing/filling site can be a "Class 100 site" or other appropriately sterile and/or aseptic or clean room condition site to maintain a desired clean or sterility state until or during dispensing/use. Alternatively, the device can be packaged, then sterilized. The term "Class 100" means a facility that has less than 100 particles per cubic meter of clean room/space. The Class 100 standard may also refer to ISO Class 5. The term "Class 100,000" refers to a facility that has less than 100,000 particles per cubic meter of clean room/space. The clean room/space can maintain a positive-pressure environment. The positive-pressure environment is configured to operate so that, upon entrance into the space, air flows out of the clean room, limiting the possibility of contaminants entering the clean room. Equipment to provide the desired class, such as, for example, Class 100 status include, for example, Class 100 laminar flow workstations, Class 100 laminar flow exhausting hoods, HEPA-filters and the like. The term "sterile or clean" extraction surface" refers to that part of the dose container that has or maintains a desired cleanliness and/or sterility. In some embodiments, to do so, the surface may be sealed or otherwise protected from exposure to environmental conditions until and/or during use.

The term "dose data indicia" refers to external markings that identify one or more of a dose amount, a medicament type, a shelf life or "use by" date, a production date, a patient name or patient-specific identifier. The dose data indicia can include machine-readable indicia (such as optic encoded "bar" code) and/or human readable alphanumeric indicia or graphic designs or symbols.

The term "dose" refers to both multi-dose and unit dose amounts. The unit dose amount may be given in a plurality of temporally close sub-dose injections for patient comfort. As a non-limiting example, a unit dose container can include about 0.6 ml of liquid medicament. The 0.6 ml amount can be dispensed as three sub-bolus injections of about 0.2 ml each of the unit dose amount in a suitable manner. The injection may be, for example, administered intradermally (ID), subcutaneous (SC), intravenous (IV), intramuscular (IM), and the like. The term "cryogenic" refers to very low temperatures, typically below 0° C.

The term "ultra-low temperatures" refers to temperatures at or below about $-40°$ C., typically between about $-70°$ C. to about to about $-196°$ C. In some embodiments, the liquid medicament is frozen and stored in a dose container for at least a portion of its storage life at ultra-low temperatures between about $-120°$ C. to about $-196°$ C. The liquid medicament in the dose container may be held in a freezer and/or coolant chamber at a temperature of between about $-120°$ C. to about $-196°$ C., typically between about $-120°$ C. to about $-150°$ C., for at least some portion of its storage and/or shelf-life, prior to use. The liquid medicament can be shipped in $LN_2$ (liquid nitrogen), $LN_2$ vapor and/or on dry ice. For some embodiments, the medicament can be held at temperatures between about $-70°$ C. to about $-95°$ C., during a portion of its life (including, for example, during shipment). The dose container may be held directly in the liquid nitrogen (at about $-196°$ C.) or in vapor, associated with the liquid nitrogen, at a temperature of about $-150°$ C. The liquid medicament in a dose container (with or without a medicament cartridge) can be shipped in a frozen state as a package that may include a bath of liquid nitrogen or liquid helium, liquid nitrogen vapor, dry ice or combinations of same at ultra-low temperatures. The liquid medicament can be held frozen, typically at ultra-low temperatures, until just prior to administration to a patient. The liquid medicament can be stored for days, weeks, months or even years at the ultra-low temperature(s) and shipped in a frozen state.

In some particular embodiments, the liquid medicament can be frozen and thawed proximate in time to a planned delivery, such as within about one hour between the thaw and injection(s), typically within about 1 hour to about 30 minutes. The liquid medicament can be held at different cryogenic and/or ultra-low temperatures during processing, storage and/or shipment.

In some embodiments, the liquid medicament (referred to by element 25 below) can be any medicament that is administered in liquid form; in one embodiment it is an aqueous medicament, and in another embodiment it is a non-aqueous medicament. The administration is typically via injection within or between layers of the skin (intradermally), but other injection sites or non-injection administration (such as subcutaneous, intramuscular, intravenous, etc. . . . ) may also be possible.

In particular embodiments, the medicament comprises a vaccine, such as a cell-based vaccine, that can be derived based on a patient's own cells or using donor cells. The cell-based vaccine medicament may be held at temperatures that are less than about $-70°$ C., typically between about $-70°$ C. to about $-196°$ C., and more typically at temperatures that are between about $-150°$ C. to about $-196°$ C., for a major at least a portion of the shelf life of the product. The medicament is then thawed proximate in time and prior to administration.

In some embodiments, the medicament can include certain types of advantageous cells that act as vaccines or other medicaments (for example, antigen presenting cells such as dendritic cells). The dendritic cells may be pulsed with one or more antigens and/or with RNA encoding one or more antigen. Exemplary antigens are tumor-specific or pathogen-specific antigens. Examples of tumor-specific antigens include, but are not limited to, antigens from tumors such as renal cell tumors, melanoma, leukemia, myeloma, breast cancer, prostate cancer, ovarian cancer, lung cancer and bladder cancer. Examples of pathogen-specific antigens include, but are not limited to, antigens specific for HIV or HCV. The liquid medicament can include other cell-based medicaments, including stem cell medicaments.

Turning now to the figures, FIG. 1 shows a cross section of an exemplary medicament delivery device 10. The device 10 includes a medicament cartridge 15 with a storage chamber 15c sized and configured to hold a dose container 20 therein. The device 10 also includes a plunger chamber 40 with an integral plunger 50. The plunger chamber 40 merges into a syringe port 60 that is closed via a dam 61 prior to use.

As shown, the cartridge 15 can include an internal needle 53 with a lumen that can pierce, puncture or otherwise enter the dose container 20. The needle 53 may axially translate to contact the dose container 20. Alternatively, the container 20 may translate to contact the needle 53 or both components may translate to cause the contact (not shown). Also, to inhibit the internal needle 53 from inadvertently entering into the dose container, the cartridge 10 can include a releasable safety stop member 55. Alternatively, or additionally as shown, an internal wall 31 can be configured to inhibit the internal needle 53 from inadvertently contacting the dose container 20.

As also shown, the needle 53 can reside proximate a first end portion of the cartridge 15 and, as shown with reference to FIGS. 2 and 3, the needle 53 can translate from a non-use retracted position (FIG. 2) to an operative extraction position (FIG. 3), wherein the needle 53 pierces and enters the dose container 20 to be in fluid communication with the liquid medicament 25 during extraction of the medicament.

As shown in FIG. 1, the safety stop member 55 can be configured as a clip that resides between a plunger tab 56 and the cartridge housing and blocks any axially forward movement of the needle 53. To remove the stop member 55, a user can pull, tear, twist, pop or otherwise remove or disengage the stop 55 to allow the plunger 56 to axially translate, thereby moving the needle 53.

In some embodiments, the needle 53 can be attached to the plunger 50. The plunger 50 can be prevented from engaging prematurely by the safety stop member 55, which can be removable and reside between a plunger tab 56 and a static portion of the plunger wall 45. Upon removing the safety member 55 the plunger 50 can be engaged by moving the plunger 50 axially and proximally toward the separating wall 31. Other means for preventing the plunger 50 and/or needle 53 from movement to inhibit inadvertent engagement can be utilized, including for example, both removable and non-removable components, including a retracting device, a removable component (e.g., a pin or a collar, etc.), or a twist mechanism that requires partial rotation of a mechanism or multiple components can be employed.

As shown in FIGS. 1-3 (and elsewhere herein), the dose container 20 can be an elongate container, such as a substantially tubular container. It is noted that the base reference number, e.g., "20" will be used to indicate a component generally, and subsequent embodiments may be represented with a suffix such as 20', 20", and the like in the description that follows. Features described with respect to one embodiment may be combined with a different embodiment. The cartridge chamber 15*c* can have a chamber wall 16 that substantially, or entirely, encloses the dose container 20. That is, as shown in this embodiment, the dose container 20 is a substantially cylindrical tube that is bounded by the medicament cartridge storage chamber wall 16. In embodiments of the invention, the size and shape of the cartridge storage chamber 15*c* is designed to substantially match whatever container containing a medicament is to fit inside. In such an embodiment, the chamber 15*c* can be sized and configured such that a medicament dose container 20 snugly fits inside with little tendency to move around, although this arrangement may vary. Further, spacer components can be used to provide the desired orientation and desired loose or snug fit. In some embodiments, the dose container 20 is cylindrically designed to the dimensions of the medicament storage chamber 15*c*; however, other dimensions could also be employed as desired.

While in the illustrated embodiment the medicament cartridge storage chamber 15*c* is formed in one piece, it is also possible that the cartridge 15 can comprise two or more matable components or comprise a non-enclosed frame, which merely supports and/or protects the dose container 20 rather than fully enclosing it. Combinations of a frame holder and an enclosure cartridge may also be used as will be discussed further below. In any event, the device 10 and the dose cartridge 15 (whether the enclosure or frame configuration) can have a body with greater rigidity than that of the dose container 20, and is configured to substantially enclose the dose container therein.

Where the dose container 20 (and optionally, the cartridge 15) is kept under freezing conditions, appropriate materials for the dose container are used. For example, polyvinyl chloride (PVC), a Class VI, medical grade TPE tubing, such as C-Flex®, polypropylene, polyethylene, polycarbonate and polystyrene are examples of materials for the containers which may be suitable for the medicament and cryogenic storage temperatures. The containers 20 can be extruded as a length of tubular stock that can be filled, sealed and separated at intervals to capture the dose of medicament during manufacture. Other fabrication methods may also be employed. An exemplary length is less than 20 cm, and is typically between about 5-10 cm, an exemplary wall thickness for the container 20 is between about 1/16 inch nominal. A primary lumen diameter or cross-sectional width for the container 20 is between about 3/16 inch OD (outer diameter) and 1/8 ID (inner diameter), nominal.

In some embodiments, the dose container 20 can be fabricated (extruded or molded) as a continuous length of tubing that forms a portion of a single-use disposable manufacturing system (not shown). The tubing can be wrapped around a tower or other cooled substrate configuration. The tubing can be filled with the liquid medicament by flowing the medicament therein into the tubing. The tubing can be separated and sealed at both ends in situ after the dose is filled in the tubing to define the loaded medicament dose container. Both end portions of the sealed tubing can include edges compressed onto itself to seal together via heat seal, radiofrequency seal, or other suitable sealing means (see, e.g., FIGS. 4A, 5A, 6A).

The dose container 20 can be frozen and/or stored independent of the cartridge 15 or, in another embodiment, the delivery device 10 with the dose container 20 and cartridge 15 are frozen as a single unit. As shown in FIG. 1, the dose container 20 has sidewalls 21 and opposing end portions, 22, 23, which (for end insertion embodiments) can be described as insertion end 22 and opposing end 23. In this embodiment, medicament cartridge 15 is shown containing a thawed dose of liquid medicament 25.

In FIG. 1, the dose container 20 is positioned inside the medicament storage chamber 15*c*, with the insertion end 22 toward the center of the delivery device 10 and the back end 23 toward cartridge chamber opening 28. In order to optionally close and/or seal the cartridge 20 within the chamber 15*c*, an end stopper 29 can be positioned in the cartridge chamber opening 28. The end stopper 29 can be merely pushed into the opening and held in place by friction. Other sealing means could be used to seal the chamber opening 28 including a screw threaded device, a one way locking seal, O-rings, lip seals, cup seals, gaskets or the like. Alternatively, it could include the chamber 15 having a diaphragm or sealant that closes upon the insertion of dose container 20, or the seal could be incorporated as part of the medicament cartridge itself. Seal configurations are well known to those of skill in the art.

The dose container 20 can be placed in the chamber 15*c* through an open end in the cartridge body 15 by any convenient means, such as via manual sliding placement or automated loading by gravity, force or other insertion means. Where frame-type cartridges are used, the frame components can pivot or attach after inserting the dose container in the holding chamber 15c, and the dose container 20 can be placed via top or side loading configurations.

In order to maintain suitable sterility of the medicament during the transfer, delivery and/or injection process, the cartridge chamber 15c, the end stopper 29 and any surface or component that the medicament 25 can come into contact with can be sterilized. Likewise, the dose container 20 can also be sterilized prior to filling and then a medicament 25 added. In order to keep the outer surface of the container 20 sterile and/or aseptic, the container 20 can also be stored in a sterile outer wrapping or package, which is removed (via sterile technique) just prior to or during insertion of the container 20 into the storage chamber 15. It may also possible to sterilize the medicament cartridge 15 and/or external surfaces of the dose container 20 with medicament 25 inside, but this may have some difficulties for some liquid medicaments, such as, live cell vaccines and may only be appropriate in certain circumstances.

As noted above, the end of the storage chamber 15c opposite the cartridge chamber opening 28 can include a separating wall 31. The wall 31 can include a needle throughput entry path, which is shown in FIG. 1 as a throughput aperture 32. Other throughput entry paths may also be used such as, for example, a preferentially weaker portion of the wall 31 that is configured to allow the needle 53 to pierce upon translational engagement of the plunger 50. It might also include a thin sealant or resilient material in the wall 31 that forms a septum or other means of isolating but allowing the needle to pass through the wall 31. In the embodiment shown in FIG. 1, the separating wall 31 is positioned at an angle relative to the storage chamber wall 16. It is shown at an angle of about 45 degrees, although other angles including perpendicular to wall 16 (i.e., substantially vertical for the orientation of the dose container 20 shown in FIG. 1). By angling toward the medicament container 20, the separating wall 31 can help keep the medicament container 20 positioned snugly within the medicament storage chamber 15c and can orient and align the dose container insertion end 22 toward the needle entry path 32 for eventual penetration by the internal needle 53.

The plunger chamber 40 resides at one end portion of the delivery device 10. The plunger chamber 40 can be bounded by the separating wall 31 and the plunger chamber walls 45. The plunger chamber walls 45 can be an extension of and/or contiguous with the medicament storage chamber walls 16. As shown, the plunger chamber walls 45 have a tapered wall portion 46. The tapered wall portion 46 (which can be described as a "neck") can be used to transition from a plunger chamber 40 that has a different diameter than the medicament storage chamber 15. However, the storage chamber 15c and the plunger chamber 40 can be the same size or different as appropriate, and the chamber 15c can be larger or smaller than the chamber 40.

The plunger chamber 40 has a plunger chamber opening 48 for placement of the translatable plunger 50. The plunger 50 has an internal fluid chamber 52. The needle 53 is in communication with the fluid chamber 52 and positioned such that, when the plunger 50 is advanced, the hollow needle 53 extends axially to pass through the path 32 and pierce the insertion end 22 of the medicament dose container 20 such that the hollow needle 53 is then also in fluid communication with the medicament 25 contained in the medicament container 20.

In some embodiments, the plunger chamber 40 can be sealed to the plunger chamber walls 45. In those embodiments, the chamber 40 can include a sealing means. In the embodiment shown, the sealing means includes a plunger seal 54, which is shown as an O-ring. Other sealing means known in the art could also be used such as, for example, lip seals, cup seals, gaskets, metal seals, and the like. In some embodiments, the sealing means can include precision-fit matable cooperating components.

As shown in FIG. 3, the device 10 can be configured to releasably engage a syringe 63 for transfer of the medicament 25 to the syringe 65. The syringe 63 can be engaged prior to removal of the stop member 55 and/or advancement of the plunger 50. As shown, the device 10 has a syringe fitting 60 that can sealably attach to an end portion of the syringe 63. In the embodiment shown, the syringe fitting 60 comprises a female leur lock fitting and the syringe 63 can include a matable male leur lock fitting 64. However, other means of attaching a syringe are known and can be used, including for example, a taper push-fit, a screw/threaded fitting or the like. Inside the syringe fitting 60 is an optional break-through dam 61. The dam 61 can seal the fluid chamber 52 until attachment of the syringe 63 to the fitting 60.

FIG. 3 illustrates the plunger 50 axially translated to place the needle 53 in the dose container 20 and the syringe 63 attached and in position to receive the medicament 25 from the dose container 20. In operation, the dose of medicament travels from the dose container 20 through the needle 23, into the plunger chamber 40, then out into the syringe 63 and into the syringe chamber 65. Syringe 63 is shown with its syringe attachment means 64, a male luer lock, in place in the syringe fitting 60. The break-through dam 61 has not yet been broken through, indicating that the syringe 63 is not yet fully advanced into and attached to the syringe fitting 60. Upon full engagement, the break-through dam 61 will be opened (typically without creating free-floating debris), thus leaving the fluid chamber 52 in fluid communication with syringe chamber 65. The safety strip 55 of FIG. 1 can be removed, and the plunger 50 is in its most proximal position, fully engaged with the plunger tab 56 now all the way up against the plunger chamber wall edge 70. The medicament 25 can be drawn into the syringe chamber 65 then by any convenient means such as, for example, by flow, suction or the like. After removal of the syringe 63, the delivery device 10 can safely be disposed without the need to handle the medicament cartridge 20.

The device 10 can define a unitary integral assembly of the cartridge 15, the plunger 50 and the syringe attachment 60 that, with the container 20, is a unit dose single-use disposable device. Although not shown, the syringe 63 is configured to withdraw a portion of the liquid medicament, then communicate with an injection needle that is configured to inject the withdrawn portion in the first syringe into a patient. The injection needle can be mounted to the syringe 63 or a different delivery syringe(s).

Turning now to FIGS. 4A and 4B, an exemplary dose container 20' is shown. In this embodiment, the dose container 20' includes an outwardly projecting extraction port 120 that can be bonded, heat-staked, ultrasonically welded, laser welded, adhesively attached or otherwise attached to the container body, typically in a clean room environment. The dose container 20' can be sterilized after filling and sealing in a clean environment. The clean environment may be a Class 100,000 or Class 10,000 (or better) clean room. The body 20b of the dose container 20' can be extruded and the end portions sealed to hold the liquid medicament therein. The end portions can be closed and sealed together in any suitable manner, such as, for example by employing RF sealing processes. A sealant 125s can reside over the port 120 to seal an access channel 120ch extending from the port 120 to a sterile and/or clean extraction/exit surface 125 of the container 20'. The sealant 125s can be a film that can be punctured or removed to expose the clean and/or sterile extraction surface 125. As shown, the end portions of the container 20' can include substantially flat regions 121 that may be used to place, typically imprint, dose data indicia 122. Optionally, dose data indicia may also or alternatively be placed on the outer wall 120w of the projecting port and/or the band 120b portion of the port 120.

The port 120 can be configured so that the extraction surface can reside proximate an end portion of the dose container 20' adjacent a seal edge of the dose container 20'. The port 120 can be configured as a female luer lock attachment configuration that can releasably attach to a male luer lock attachment member (not shown). Alternatively, the port 120 can reside in a dispensing cartridge 15 that defines a delivery channel to an injection syringe or that defines a direct injection needle that is in fluid communication with dose container medicament via the port 120 (also not shown).

FIGS. 5A and 5B illustrate an alternative dose container design 20". In this embodiment, the dose container includes a substantially planar base 130 and a film seal 131. The base 131 can provide improved heat transfer during freeze and thaw. The film seal 131 can be applied, typically at least to the substantially planar base 130, via heat-shrinking, bonding, heat staking, ultrasonic welding, adhesively or other suitable manner. The film seal can be applied to enclose or cover the entire dose container 20" or a selective portion thereof, where a clean and/or sterile surface is desired to be preserved for access during dispensing. The film seal 131 can be applied during extrusion of the container body 20b, or after extrusion, but typically before filling with the liquid medicament, although the film, particularly if sterile before application, can be applied after the liquid medicament is sealed in the container 20". Typically, the film 131 is applied so as to define or maintain a clean and/or sterile surface on the dose container 20".

The dose data indicia 122 can be placed on the planar base 130 and/or outer film 131. The film can comprise a laminate structure of, for example, foil and polymer and/or multiple polymer layers. The film may be in communication with a tab that allows an operator or device to pull open the film. The film may include or be used to attach a substrate with increased rigidity relative to the film to the container body 20b. The film 131 can be stripped back, peeled, punctured or otherwise removed or penetrated during dispensing of the medicament 25 from the container 20" to expose or allow access to the sterile and/or clean surface and the underlying medicament in the dose container 20".

FIGS. 6A and 6B illustrate another dose container 20'''. In this embodiment, the dose container includes axially extending wings 140 that project beyond the bounds of the primary container body 20b defining a primary lumen 75. The wings 140 may each have the same outward length (as shown) or can be different. The wings 140 can extend along substantially the entire axial length of the container 20" or, in some embodiments, reside along a portion of the length or even as one or more axially extending discrete segments (not shown). The container 20''' shown has a substantially planar base 142. The wings 140 in this embodiment can reside above the base 142 at substantially radial (diametrically) opposed locations on the container body 20b. More than one wing 140 may extend off one or both sides of the container (not shown) and the wings 140 may be offset or asymmetrically extend off the primary body 20b. The wings 140 may be used to hold the dose container 20''' in a medicament delivery cartridge 15. The profile of the dose container may provide positive alignment for insertion and/or precise orientation and positioning in a medicament delivery or transfer cartridge 15 for extraction and/or dispensing. Dose data indicia 122 can be placed on one or more of the wings (top and/or bottom surfaces) and/or the outer wall of the secondary lumen 175w.

As also shown in FIGS. 6A and 6B, the dose container 20''' may include a plurality of lumens, shown as a primary lumen 75 and a secondary lumen 175. However, it is noted that the dose container 20''' may also be configured with only the primary lumen 75.

The lumens 75, 175 may be in fluid isolation from each other, at least during storage prior to administration of the medicament to a patient. The secondary lumen 175 can have a thinner wall thickness than that of the primary lumen 75 and may also have a smaller cross-sectional area. The lumens may also be of different cross-sectional profile geometric shapes, i.e., substantially square, rectangular, triangular, arcuate, curvilinear, and the like. The wall 175w of the secondary lumen 175 can have a wall thickness that is between about ⅓ to about ⅔ less than the wall thickness of the thinnest part of the wall 75w defining the primary lumen 75. The secondary lumen 175 can seal a sterile/clean (typically Class 100) surface 125 therein that can be exposed by cutting away or otherwise accessing the dose container primary lumen through a wall defining the secondary lumen.

The secondary lumen 175 may have a volume that is between about ½-¼, typically between about ⅓- to about ¼, of that of the primary lumen 75. In particular embodiments, the secondary lumen 175 may have a cross-sectional area of between about 1 mm to about 5mm, typically about 2 mm. The orientation of the primary lumen 75 and the secondary lumen 175 can be reversed. A tertiary lumen may also be used above the secondary lumen 175 or on the container body 20b away from the secondary lumen 175.

FIGS. 7A and 7B illustrate a dose retainer assembly 90 that is configured to sandwich the dose container 20'''' (or other dose container configurations) to trap and hold the dose container 20'''' snugly therein by clamping against the wings 140 of container 20''''. As shown, the dose retainer assembly 90 includes a clamp member 91 and a base member 93. The two members 91, 93 attach to trap the dose container 20'''' therebetween. The dose container 20'''' is similar to that shown in FIGS. 6A and 6B, but the wings 140 extend outwardly from the base 142. The dose container 20'''' shown in FIG. 7C includes the primary and secondary lumens 75, 175, but a single lumen (or other multi-lumen) configuration may also be used.

As shown in FIG. 7C, the dose retainer assembly 90 is configured with an axially extending window or gap space that allows the upper portion of the dose container 20'''' to project above the bounds of the clamp and base members when assembled. That is, as shown, the secondary lumen 175 and an upper portion of the primary lumen 75 reside above the clamp member 91 as well as above the bounds of a housing 95 that engages with the base 93 to hold the dose container 20''''. In some embodiments, the dose container 20'''' is loaded or assembled to the dose retainer assembly 90 prior to cryogenic storage and thereafter defines a unitary body that prior to administration is placed in a dispensing or transfer delivery cartridge 15. The dose retainer 90 can contain dose data indicia 122 and may comprise a clear or transparent polycarbonate or polypropylene material, which may be particularly suitable for ultra-low temperature storage and/or cryogenic storage.

The outer surfaces of the frame of the dose retainer assembly 90 may include primary and/or secondary dose data indicia 122 or the entire labeling for the medicament (rather than the dose container 20', 20", 20''', 20'''' and the like). Advantageously, in some particular embodiments, the dose retainer assembly 90 does not require seals or moving parts that may fail due to (prolonged) exposure to ultra-low temperatures.

FIGS. 8A-8E illustrate that any of the dose containers 20, 20', 20", 20"', 20"" can be placed in a medicament cartridge 15 with a roller 150 used to press against the dose container to force the medicament out of the container into either an injection needle or into a syringe for subsequent transfer or injection. This embodiment is shown with respect to multi-lumen dose containers, but can be used with single lumen containers as well, particularly where a sterile surface is available at extraction. The roller 150 can be configured to provide reliable dispensing volume(s) and suitable evacuation of the dose container. The roller 150 may (elastically) deform the dose container 20 during dispensing as it presses against the body of the container.

FIGS. 8A and 8B illustrate the multi-lumen dose container 20"' with the base 142 contacting the roller 150. The roller may be configured to press against a side rather than a top or bottom (and multiple cooperating rollers may also be used) (not shown). The projecting profile 20p (with the wings 140) can be used to precisely orient and firmly retain the container in the cartridge for alignment with the roller. The roller 150 can cooperate with the dose container to generate linear peristaltic pumping action. See, e.g., U.S. Pat. Nos. 5,924,852 and 5,980,490, the contents of which are hereby incorporated by reference as if recited in full herein (with embodiments of the invention employing a moving roller and substantially stationary target).

FIG. 8B also illustrates a needle 53, 153, which can be an internal needle 53 (e.g., a needle that resides within the bounds of the cartridge 15) or an external needle 153 that is extends outside the bounds of the cartridge. The external needle 153 may be associated with a cooperating syringe (not shown) or may be attached to the cartridge 15 for direct injection to a patient from the dose container 20. In any event, the secondary lumen 175 can be opened, separated and/or removed, and the needle 53, 153 can pierce the exposed surface of the wall of the primary lumen 75.

FIGS. 8C and 8E illustrate that the projecting portion of the dose container 20p can contact the roller 150. FIGS. 8C and 8D also illustrates that the roller 150' may optionally have a shaped or profiled surface. FIG. 8E illustrates that the roller 150 can press against both the secondary and primary lumens 175, 75 to expel the liquid medicament. The wings 140 can be used to firmly retain the container 20 in cooperating alignment with the roller 150.

FIGS. 9A and 9B illustrate a delivery/transfer medicament cartridge 15 that has an extraction/dispensing mechanism. In this embodiment, the extraction/dispensing mechanism comprises a cutting member 180 and an internal needle 53. This embodiment is illustrated with a portion of the cartridge 15 removed or omitted for clarity of discussion on certain internal features. As shown, the cartridge 15 is configured to receive and hold the dose retainer 90 with the dose container 20"". The dose container 20"" is held so that the secondary lumen 175 resides above the plane of the cutting member 180. The cutting member 180 can comprise an axially translating blade. The internal needle 53 can angle downwardly toward the dose container 20"". The needle 53 may also be configured to translate axially, either independently or with the cutting member 180. In some embodiments, the needle 53 can translate substantially in concert with the cutting member 180. In operation, the cutting member 180 is configured to cut or slice into the wall of the secondary lumen 175w to expose the primary lumen surface prior to entry by the needle 53 so that the needle then pierces the wall of the primary lumen at the clean surface location under the opened wall segment 175w. As such, the internal needle 53 and associated components are in fluid communication with the medicament in the dose container primary lumen 75 so as to be able to direct, withdraw or extract the liquid medicament in a clean, substantially sterile manner. In some embodiments, a portion of the secondary lumen wall 175w may be configured to tear away, and the cutting member 180 may be configured as a tearing member that cooperates with the wall 175w (not shown).

FIGS. 10A-10C illustrate one embodiment where a portion of a cartridge 15 can undergo a series of operations to cut, then pierce, the dose container 20"". In FIG. 10A, the cutting member 180 is shown retracted. As shown, the cutting member 180 is a substantially planar blade that is oriented to translate substantially horizontally. FIG. 10B illustrates the cutting member 180 cutting or slicing through a wall of the secondary lumen 175 exposing a clean and/or sterile surface 125. FIG. 10C illustrates the needle entering the primary lumen 75 at the clean surface 125 ready for dose withdrawal or extraction. In some embodiments, the cutting member 180 can include a window 180w (FIG. 9B) and the needle 53 can extend through this window to access the exposed surface 125 and enter the primary lumen 75.

FIG. 11 illustrates an exemplary delivery/transfer device 10 with a medicament cartridge 15. As shown, the device 10 can be a direct injection device that is configured to directly inject at least one dose (as a single or a series of sub-doses) into a patient. However, the device 10 can be modified to be used with a syringe or other indirect delivery device.

As shown in FIG. 11, the cartridge 15 has a body 15b with a window 15w that allows a user to visually assess the dose container 20"". Outside the cartridge 15, the dose container 20"" (for this embodiment and others described herein) may be flexible but have sufficient rigidity to retain its shape with or in the absence of the liquid therein. The dose container 20"" may also be visually transmissive to allow a user to ascertain visually a quantity of liquid therein by looking at the window 15w. The cartridge 15 can include a roller 150 configured to contact and roll against the dose container 20"" to dispense the liquid from the dose container. The cartridge 15 can also include an extraction/dispensing housing 188 that can translate toward the dose container 20, an external injection needle 153 in communication with the extraction housing 188 and a plunger 200 that can be used to activate/control the dispensing/extraction. The cartridge 15 can include a safety member 55, shown as a removable clip that spans the cartridge body 15b to prevent axial translation of the extraction housing 188. As shown, the roller 150 is in communication with a roller guide 151 that can include a rod 151r.

As shown in FIGS. 12 and 13, the roller guide 151 is supported by the cartridge body 15b in a manner that allows the roller guide 150 to travel with roller 150 axially aligned with and firmly contacting the underlying dose container 20"" with a desired pressure/force. In this embodiment, the dose container 20"" is oriented so that the projecting portion 20p faces the roller 150, with the secondary lumen 175 closer to the roller 150 than the primary lumen 75. Single and other multi-lumen containers may also be used (not shown). The roller guide 151 can be keyed to a pair of spaced apart rails 15r defined by the cartridge body so that the roller 150 only moves unidirectional (axially toward the dose container 20). The rails 15r can include teeth 15t (FIG. 13) that engage a pawl 151p associated with the roller guide arms 151a to define a ratchet mechanism to control directional movement. The roller 150 can be formed of a substantially rigid material, such as, for example, a rigid high density polyethylene (HDPE) a glass-filled polymer, a resin-reinforced composite or other suitable material, that is not deformable when used to apply the desired pressure.

As shown in FIGS. 12 and 13, the cartridge 15 can also include a return spring 210 that biases the plunger 200 to return to a home position. The spring 210 resides between a static shelf 15s in the cartridge body 15b and a ledge 201 on the plunger 200 such that, when the plunger 200 is depressed, the spring 210 compresses against the shelf 15s in the cartridge 15. When pressure is removed, the spring 210 forces the plunger 200 back to the home position. The cartridge 15 can also include a dose retainer cavity 15c and a spring-loaded dose retainer clip 215 that resides in an end portion of the cavity 15c. The clip 215 is biased forward to push axially snugly against the dose retainer 90 when loaded (FIGS. 15A and 15B).

Referring to FIG. 14, the external injection needle 153 can be in communication with a needle luer lock 154 that can allow a user to place or replace the needle 153 at a use site. The injection needle 153 can be single-use disposable (i.e., disposable after a single injection). Alternatively, the injection needle 153 may be sterilized and reused while attached.

FIG. 14 illustrates the extraction/dispensing end portion of the cartridge with the housing 188 (FIG. 11) removed. As shown, the cartridge 15 can include a needle guide 53g that directs or controls the movement trajectory of the internal translatable needle 53. Similarly, the cartridge 15 can include a blade guide 180g to guide the translation of the cutting member 180. The needle guide 53g can include arms 53a that extend through slots 17 in the cartridge 15. The slots 17 can be curvilinear and angle downward in the direction of the dose container 20.

FIGS. 15A and 15B illustrate a dose container 20'''' held in a retainer 90 ready for insertion (after thaw) into the cartridge cavity 15c. FIGS. 16 and 17 illustrate the cartridge 15 after the retainer assembly 90 is in position in the cavity 15c, with the dose retainer clip 215 pressing axially against the dose retainer assembly 90. FIGS. 15B and 17 also illustrate that the internal needle 53 terminates into a fluid path in the housing 155 that engages the luer-lock member 154 and during operation is in fluid communication with injection needle 153. The luer-lock fitting 154 may include a one-way valve 154v so that a user can replace the needle 153 for another injection without allowing air into the flow path.

Figure 18:
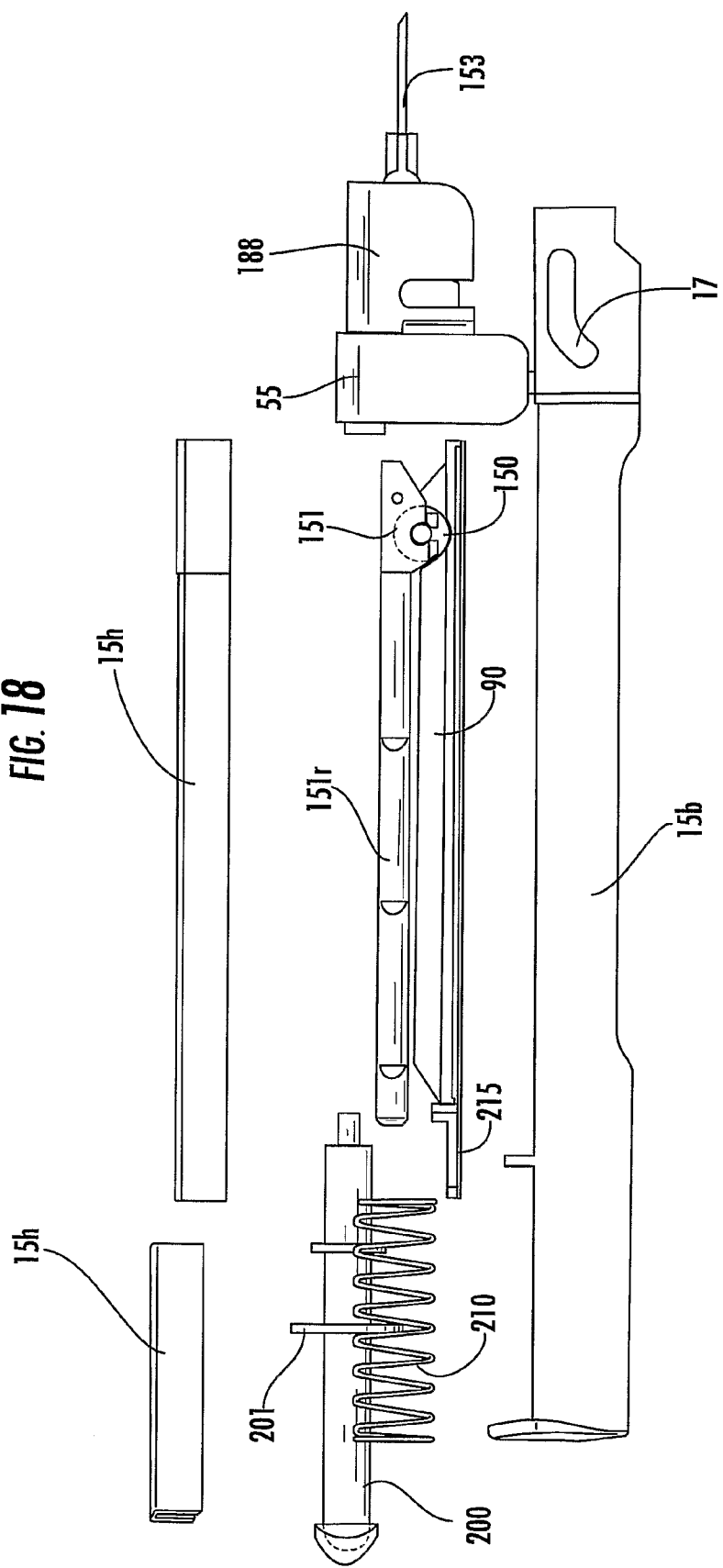
FIG. 18 is an exploded side view of components of the medicament cartridge and dose container shown in FIGS. 15A and 16.

FIGS. 18 and 19 are exploded views of components that can be used to form the medicament cartridge 15. As shown, the cartridge 15 includes a primary cartridge body 15b, an extraction housing 188, stop member 55, the roller 150 with roller guide 151, the dose retainer assembly 90, the plunger 200, with spring 210, and cartridge housing components 15h that mate to cartridge body 15b. The housing components 15h (and cartridge body 15b) may be visually transmissive.

As shown in FIGS. 20B, 21B and 22B, once the safety stop member 55 is removed from between a tab 189 associated with the extraction housing 188 and a tab 18 extending from the cartridge body 15b, the extraction housing 188 (and cutting member 180 and needle 53) can translate axially forward. FIGS. 20A, 21A, and 22A illustrate the positions of the cutting member 180 and the needle 53 as they move forward to cut and pierce the dose container 20''''. As described above, the secondary lumen 175 maintains an enclosed clean and/or sterile surface 125 that can be penetrated during extraction/dispensing of the liquid medicament.

Generally described, the plunger 200 cooperates with the roller guide rod 151r to serially dispense a plurality of fixed volume amounts of the liquid medicament by rolling the roller 150 forward along the dose container, thereby compressing the lumen 75. The fixed volume amounts can be substantially constant (typically within about +/−5%). The roller 150 can be configured to apply a substantially constant compression, substantially pressing the primary lumen 75 (and the secondary lumen where used) flat to eject the fixed volumes. The height of the roller 150 can be sufficient to generate sufficient compression to evacuate substantially the entire liquid amount from the dose container in a plurality of strokes.

Figure 23A:
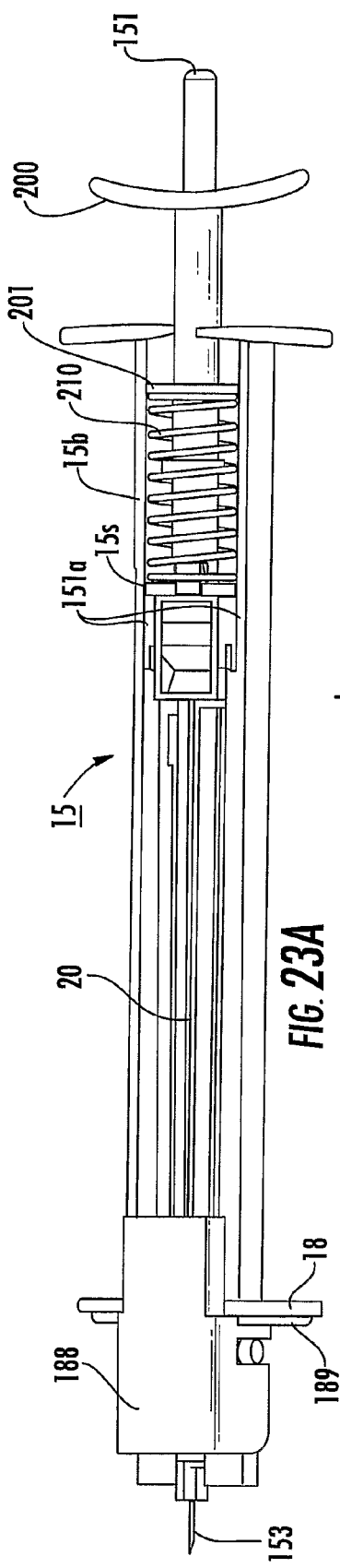
FIGS. 23A-23C are side views of the device shown in FIGS. 11-14, illustrating an exemplary priming sequence to extract/dispense medicament, then reset the plunger according to some embodiments of the present invention.
Figure 23B:
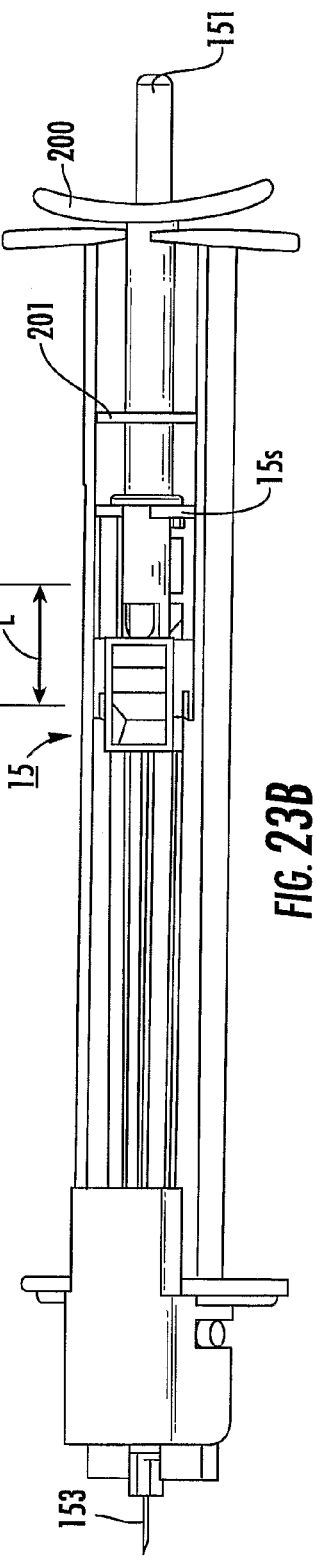
Figure 23C:
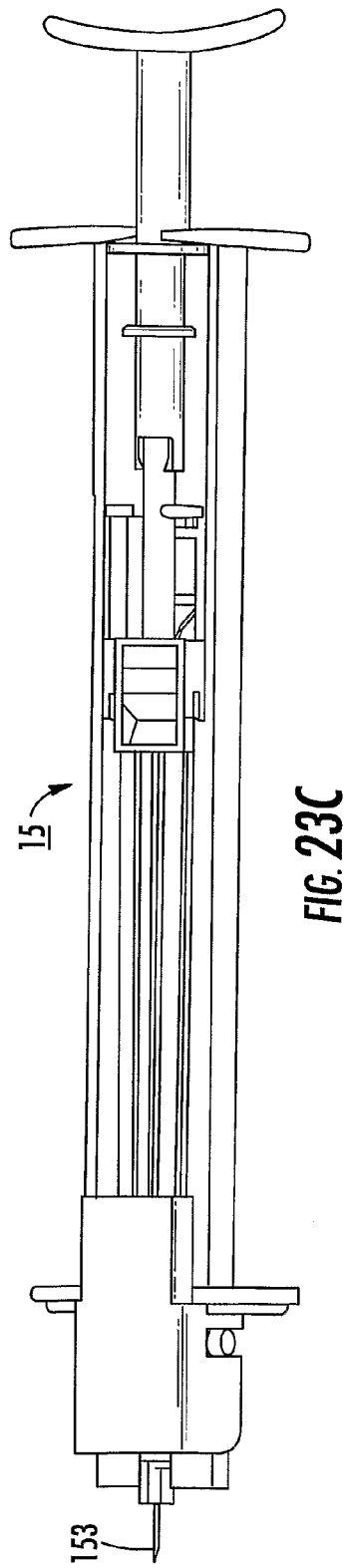

After the safety stop 55 is removed and the dose container is opened as shown in FIGS. 20A, 21A, and 22A, the cartridge 15 can be primed for active dispensing. FIGS. 23A-23C illustrate a series of configurations that the cartridge 15 and its components travel through as an operator primes the cartridge 15 to be ready to dispense and resets the plunger 200 for dispensing. The spring 210 is omitted in FIGS. 23B and 23C. The "priming" operation can eject or extract a first volume amount of the liquid from the dose container 20 into the flow path so that a portion of the flow path downstream of the dose container 20 (at least the piercing needle 53) is substantially full but without directing an undue amount of liquid (if any) to exit the injection needle 153.

The plunger 200 in cooperation with the roller guide rod 151r moves the roller 150 through a plurality of serial strokes. The plunger 200 can engage the guide roller rod 151r at different locations, typically at the notched locations (FIGS. 18, 19), starting closest to the roller 150 and progressing to the farthest location along the rod to push the guide roller rod 151r with the roller 150 progressively more forward toward the injection needle 153 while the roller 150 compresses the lumen 75.

FIG. 23A illustrates an initial position of the roller 150 and roller guide 151r. FIGS. 23B and 23C illustrate a post-prime, ready to dispense location of the roller 150. FIG. 23C illustrates the plunger 200 being reset for actuation of the guide rod 151 forward to begin dispensing. Because the mounting of the roller guide 151 in the cartridge body 15 employs a ratchet mechanism, the roller 150 and roller guide 151 stay in the forward location, even as the plunger 200 is translated outwardly away from them.

FIGS. 24A-24C illustrate the position of the plunger 200 and roller guide 151 at the dispense configuration of the first two (sub) doses. FIG. 24A illustrates the location of the components to dispense the first dose amount. FIG. 24B illustrates the plunger 200 being withdrawn for dispensing the second dose amount. FIG. 24C illustrates the location of the components to dispense the second dose amount. FIG. 24D illustrates the plunger 200 being withdrawn for dispensing the third dose amount. FIG. 24E illustrates the position of the plunger 200 and roller guide 151 at the dispense configuration of the third (sub) dose amount. Each of the three dose amounts may be about 0.2 ml (or 200 microliters). The roller 150 moves a stroke length "L" during the priming operation and each dispensing operation. The stroke length "L" of the initial priming step (where used) can be different from the other stroke lengths, which are typically substantially the same.

Turning now to FIG. 25, another embodiment of a medicament cartridge 15' is illustrated. In this embodiment, the cartridge 15' can include a clamp that can generate an evacuation pressure to force the liquid medicament from the dose container 20. The cartridge 15' can cooperate with an external and/or internal needle, 153, 53, respectively.

FIG. 26 illustrates yet another embodiment of a medicament cartridge 15". In this embodiment, the medicament cartridge 15" that holds the dose container 20 is configured to be in fluid communication with a fluid syringe containing biocompatible, sterile fluid 253, such as at least a Class 100 sterile gas, such as air. The syringe 250 can includes a needle 251 that can pierce one end of the dose container 20 to force the fluid 253 from the syringe 250 into the dose container 20. In response, the liquid medicament 25 exits the dose container via a second needle 53, 153 that pierces the dose container 20 at the other end. As before, the needle 53, 153 can be an internal and/or external needle. If an external needle 153, the needle 153 can be used for direct or indirect patient injection. Instead of a needle 251, a luer-lock fitting can be used to engage the dose container (not shown).

FIG. 27A is a schematic illustration of the dispensing operation of the cartridge 15" shown in FIG. 26. As shown, the fluid 253 from the syringe 250 enters (is injected into) the dose container 20 via needle 251. The fluid 253 forces the liquid from the container 20 into the needle 153 and into an associated syringe 260.

FIG. 27B is a schematic illustration of an alternate configuration of the fluid injection extraction/dispensing embodiment shown in FIG. 27A. In this embodiment, the cartridge 15" can include a flow valve 268 (which can be a one-way valve) with a micro- or nano-sized flow meter 269 that can control serial dispensing of fixed volumes. The valve 268 can be in communication with a direct injection needle 153.

FIG. 28A is a schematic illustration of a medicament delivery kit 290. The kit 290 can include, for example, a syringe of (sterile) fluid 250, a dose container with liquid medicament which may be in a frozen state and held in a cryogen bath 299, and optionally, a patient injection syringe 260 and/or medicament cartridge 15".

FIG. 28B is a schematic illustration of a sealed dose container 20 in a coolant 299 and enclosed in a thermal resistant package 300 for shipment to a use site to maintain the medicament within a desired temperature range, such as at about −40° C. or below. In some embodiments, the coolant 299 can comprise dry ice (typically at a temperature of about −78.5° C.). The internal temperature of the package 300 proximate the dose container can be between about −70° C. to about −110° C., such as between about −70° C. to about −95° C. In some embodiments, the coolant 299 can comprise a cryogenic liquid, which can hold the container 20 at desired temperatures during shipment. The sealed dose container 20 can be held in vapor associated with the bath and/or in the liquid bath itself. Exemplary temperatures in the package 300 can be between about −120° C. to about −196° C. In some embodiments, the container 20 can be have a temperature between about −70° C. to about −150° C. in the package 300. In some embodiments, the dose container 20 and medicament therein can be held frozen at, for example, between about −70° C. to about −196° C. In some embodiments, the dose container and medicament are held at between about −120° C. to about −196° C., typically between about −150° C. to about −196° C. The cryogenic liquid can comprise liquid nitrogen, which under normal atmospheric pressure can exist as a liquid between the temperatures of 63 K and 77.2 K (−346° F. and −320.44° F.). Combinations of coolants can also be used.

FIG. 29 illustrates yet another medicament dispensing system 10. In this embodiment, the cartridge 15 is configured to hold the dose container 20, which may be in dose retainer assembly 90. The dose container 20' can be a single lumen container with wings 140. The cartridge 15 can include an integral needle heater unit 325 that heats the needle 53, 153 that is used to withdraw the liquid medicament. As before, the needle 53, 153 can be an external or internal needle. In other embodiments, the heater unit 325 can be a portable relatively compact unit that can be included as part of the medicament delivery kit (not shown). As shown in FIGS. 30A, 30B, the needle 53, 153 is heated in a small channel 325ch in the heater unit 325 to an appropriate sterilization temperature (typically at least about 400° C.) for a desired time. The heater unit 325 may include an alert so as to notify a user when the needle has been properly sterilized. The heater unit 325 can attach to the cartridge 15'''. After sterilization, the needle 53, 153 can be advanced through the needle heater unit channel 325ch into the dose container 20'. The advancement can be carried out proximate in time to the sterilization, although not immediately, so as to allow the needle to return to a desired temperature before contacting the medicament 25. The needle 53, 153 can be sterilized in situ one or more times.

The foregoing is illustrative of embodiments of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A medicament device, comprising:
   a sealed medicament dose container having a substantially tubular body comprising a medicament that is stored frozen, then thawed into a liquid prior to administration, wherein the dose container has a longitudinally extending compressible outer wall with a perimeter having a pair of substantially parallel spaced apart long sides that enclose an interior chamber and that merge into opposing first and second closed short ends;
   a medicament dose cartridge configured and sized to snugly hold the dose container therein during extraction of the liquid medicament; and
   a dose retainer comprising a frame and a base portion, wherein the dose retainer is configured to sandwich the dose container between the frame and the base and define a unitary dose assembly adapted for cryogenic storage separate from the cartridge, and wherein the dose assembly is sized and configured to be snugly held in the dose cartridge prior to extraction of the liquid medicament.

2. A device according to claim 1, wherein the dose cartridge has a body with greater rigidity than that of the dose container and is configured to substantially enclose the dose container therein, wherein the substantially tubular body has at least one flat wing extending outward from a respective long side about a length of the substantially tubular body, and wherein the medicament dose container is between about 5-10 cm long.

3. A device according to claim 1, wherein the dose cartridge has a body with greater rigidity than that of the dose container, and wherein the frame is configured so that, when the frame is closed about the medicament dose container, the dose cartridge encases an entire outer perimeter of the dose container but is configured to expose an outer surface of the medicament dose container to environmental conditions.

4. A device according to claim 1, wherein the device is a unit dose single-use disposable device.

5. A device according to claim 1, wherein the liquid medicament is in a quantity sufficient to provide a plurality of sub-doses of about 0.2 ml each, wherein the sealed medicament container with the medicament is configured to be stored at a temperature that is below about −40 degrees Celsius.

6. A device according to claim 1, wherein the medicament comprises a cell-based vaccine, and wherein the sealed medicament container with the medicament is stored at a temperature that is less than about −80 degrees Celsius prior to administration.

7. A device according to claim 1, further comprising a portable package of liquid cryogen configured and sized to hold the unitary dose assembly in a frozen state during shipment, wherein the sealed medicament dose container with the medicament in the cartridge are held at between about (a) −70 degrees Celsius to about −95 degrees Celsius for a least a portion of a storage period or during shipment or during at least a portion of a storage period and during shipment or (b) −120 degrees Celsius to about −196 degrees Celsius for a least a portion of a storage period or during shipment or during at least a portion of a storage period and during shipment.

8. A device according to claim 7, wherein the liquid cryogen comprises liquid nitrogen.

9. A device according to claim 1, wherein the device includes an injection needle in communication with the dose container held by the dose cartridge that is configured to directly inject the medicament from the dose container into a patient.

10. A device according to claim 1, further comprising:
a first syringe that is adapted to be in fluid communication with the dose container while the dose container is held by the dose cartridge.

11. A device according to claim 1, further comprising:
a needle in fluid communication with the liquid medicament in the dose container;
a one-way flow valve in fluid communication with the needle; and
a liquid expulsion system held in the medicament dose cartridge, the liquid expulsion system comprising with a unidirectional roller configured to contact and roll against the dose container during use, the roller in communication with a roller guide keyed to a pair of spaced apart rails.

12. A device according to claim 1, further comprising a needle and a needle heater unit sized and configured to heat the needle at a dose delivery site to a temperature sufficient to sterilize the needle, wherein the needle is heated and advanced to pierce or puncture the dose container while heated.

13. A device according to claim 1, further comprising a cutting member and a needle in the cartridge whereby the dose container or the cutting member and the needle axially translate to cut the dose container to define an entry port that the needle enters.

14. A device according to claim 1, wherein the dose cartridge comprises a stepped fixed volume dispensing mechanism that includes a manually depressible plunger that communicates with a pressing member, the pressing member residing outside and in abutting contact with the dose container outer wall, and wherein the dispensing mechanism slidably advances the pressing member fixed different distances in the cartridge to dispense a plurality of fixed amounts of the liquid medicament from the dose container.

15. A device according to claim 1, wherein the liquid medicament is a cell-based vaccine provided in an amount sufficient to provide a plurality of sub-doses of about 0.2 ml.

16. A device according to claim 1, further comprising a shipping container having a cryogenic storage chamber, wherein the unitary dose assembly is held in the cryogenic storage chamber prior to insertion in the cartridge.

17. A device according to claim 1, wherein the dose container has sufficient rigidity to maintain its shape with and without liquid medicament held therein.

18. A medicament device, comprising:
a sealed medicament dose container having a substantially tubular body comprising a medicament that is stored frozen, then thawed into a liquid prior to administration, wherein the dose container has a longitudinally extending compressible outer wall with a perimeter having a pair of substantially parallel spaced apart long sides that enclose an interior chamber and that merge into opposing first and second closed short ends; and
a medicament dose cartridge configured and sized to snugly hold the dose container therein during extraction of the liquid medicament,
wherein the dose cartridge comprises a first end portion having an internal needle that does not contact a patient and is held in a non-use retracted position inside the dose cartridge during storage and is configured to translate along a fixed path inside the dose cartridge from the non-use retracted position to an extraction position whereby the internal needle pierces the dose container and is in fluid communication with the liquid medicament during extraction of the medicament.

19. A device according to claim 18, wherein the dose cartridge further comprises an external locking member in communication with the internal needle to prevent the internal needle from inadvertently piercing the dose container.

20. A device according to claim 18, wherein the dose cartridge encloses the dose container has a second end portion axially opposed from the first end portion, the second end portion being open and configured to slidably receive the dose container therein, wherein the internal needle translates inward from a location proximate the first end portion of the dose cartridge to enter the first end of the dose container.

21. A device according to claim 18, wherein the dose cartridge has a solid outer wall that encloses the dose cartridge and a second end portion axially opposed from the first end portion, the second end portion being configured to slidably receive the dose container therein, further comprising a plug member configured to sealably close the second end portion of the dose cartridge.

22. A device according to claim 18, wherein the sealed dose container is held in a sealed state enclosing the medicament that is stored frozen, then thawed into a liquid prior to administration and, in the sealed state, the sealed dose container is devoid of movable internal components that force the medicament out of the dose container, and wherein the dose cartridge first end portion is adapted to slidably receive a syringe in a manner that places the syringe in fluid communication with the internal needle to allow a dose amount of the medicament to be withdrawn by the internal needle and directed into the syringe.

23. A device according to claim 18, wherein the dose cartridge further comprises a laterally extending interior wall residing inside an outer wall of the dose cartridge between the internal needle and the dose container proximate but spaced apart from the first end portion of the dose cartridge when the internal needle is in a retracted configuration, and wherein the internal needle is configured to travel past the interior wall when the internal needle moves to an extended configuration to pierce the dose container.

24. A medicament device, comprising:
a sealed medicament dose container having a substantially tubular body comprising a medicament that is stored frozen, then thawed into a liquid prior to administration, wherein the dose container has a longitudinally extending compressible outer wall with a perimeter having a pair of substantially parallel spaced apart long sides that enclose an interior chamber and that merge into opposing first and second closed short ends;

a medicament dose cartridge configured and sized to snugly hold the dose container therein during extraction of the liquid medicament; and a syringe that is configured to withdraw a portion of the liquid medicament from the dose container via an internal needle held by the dose cartridge that longitudinally translates along a fixed path to pierce the dose container at a location that is misaligned with a longitudinally extending centerline of the dose container, then engage a separate injection needle that is configured to inject the withdrawn portion in the syringe into a patient.

25. A device according to claim 24, wherein the internal needle resides inside of the dose cartridge and travels the fixed path between defined extended and retracted positions while inside the dose cartridge, wherein the internal needle resides proximate the injection needle and translates independently of the injection needle.

26. A medicament device, comprising:

a sealed medicament dose container having a substantially tubular body comprising a medicament that is stored frozen, then thawed into a liquid prior to administration, wherein the dose container has a longitudinally extending compressible outer wall with a perimeter having a pair of substantially parallel spaced apart long sides that enclose an interior chamber and that merge into opposing first and second closed short ends;

a medicament dose cartridge configured and sized to snugly hold the dose container therein during extraction of the liquid medicament; and a first syringe that is adapted to be in fluid communication with the dose container while the dose container is held by the dose cartridge, wherein the dose container is configured to be pierced or punctured at first and second opposing end portions for extraction of the liquid medicament therein.

27. A device according to claim 26, further comprising a second syringe comprising sterile gas, and wherein the second syringe is adapted to be in fluid communication with the dose container at an opposing end of the dose container from the first syringe while the dose container is held in the dose cartridge whereby the gas pushes the liquid out of the dose container into the first syringe.

28. A device according to claim 27, wherein the cartridge further comprises at least one luer-lock configured to releasably engage at least one of the first and second syringes.

29. A medicament device, comprising:

a sealed medicament dose container having a substantially tubular body comprising a medicament that is stored frozen, then thawed into a liquid prior to administration, wherein the dose container has a longitudinally extending compressible outer wall that encloses an interior chamber with opposing first and second closed ends; and a medicament dose cartridge configured and sized to snugly hold the dose container therein during extraction of the liquid medicament, wherein the dose cartridge comprises a stepped fixed volume dispensing mechanism that includes a manually depressible plunger that communicates with a pressing member, the pressing member residing outside and in abutting contact with the dose container outer wall, wherein the stepped fixed volume dispensing mechanism slidably advances the pressing member fixed different distances in the cartridge to dispense a plurality of fixed amounts of the liquid medicament from the dose container, and wherein the pressing member comprises a roller, and wherein the plunger is in communication with the roller and a roller guide and a ratchet held in the cartridge, wherein the roller guide and ratchet cooperate to keep the roller in a forward location in the dose cartridge even when the plunger translates rearward, and wherein the plunger causes the roller to translate longitudinally to depress the compressible outer wall of the dose container to force the liquid medicament out of the dose container.

30. A medicament device, comprising:

a sealed medicament dose container having a substantially tubular body comprising a medicament that is stored frozen, then thawed into a liquid prior to administration, wherein the dose container has a longitudinally extending compressible outer wall that encloses an interior chamber with opposing first and second closed ends; and a medicament dose cartridge configured and sized to snugly hold the dose container therein during extraction of the liquid medicament, wherein the dose cartridge comprises a stepped fixed volume dispensing mechanism that includes a manually depressible plunger that communicates with a pressing member, the pressing member residing outside and in abutting contact with the dose container outer wall, wherein the stepped fixed volume dispensing mechanism slidably advances the pressing member fixed different distances in the cartridge to dispense a plurality of fixed amounts of the liquid medicament from the dose container, and wherein the pressing member comprises a roller with a curved inner surface that faces the dose container outer wall.

31. A medicament device, comprising:

a sealed medicament dose container having a substantially tubular body comprising a medicament that is stored frozen, then thawed into a liquid prior to administration, wherein the dose container has a longitudinally extending compressible outer wall with a perimeter having a pair of substantially parallel spaced apart long sides that enclose an interior chamber and that merge into opposing first and second closed short ends; and a medicament dose cartridge configured and sized to snugly hold the dose container therein during extraction of the liquid medicament;

wherein the dose cartridge comprises a stepped fixed volume dispensing mechanism that includes a manually depressible plunger that communicates with a pressing member, the pressing member residing outside and in abutting contact with the dose container outer wall, wherein the dispensing mechanism slidably advances the pressing member fixed different distances in the cartridge to dispense a plurality of fixed amounts of the liquid medicament from the dose container, and wherein the dose cartridge comprises a replaceable needle interface comprising a needle luer-lock member directly attached to one end portion of the dose cartridge and is configured to releasably accept a plurality of different needles to extend adjacent to the one end portion of the dose cartridge.

32. A medicament device, comprising:

a sealed medicament dose container having a substantially tubular body comprising a medicament that is stored frozen, then thawed into a liquid prior to administration, wherein the dose container has a longitudinally extending compressible outer wall that encloses an interior chamber with opposing first and second closed ends; and a medicament dose cartridge configured and sized to snugly hold the dose container therein during extraction of the liquid medicament, wherein the dose cartridge comprises a first end portion having an internal needle that does not contact a patient and is held in a non-use retracted position inside the dose cartridge during storage and is configured to translate along a fixed path inside the dose cartridge from the non-use retracted position to an extraction position whereby the internal needle pierces the dose container and is in fluid communication with the liquid medicament during extraction of the medicament, wherein the sealed dose container is held in a sealed state enclosing the medicament that is stored frozen, then thawed into a liquid prior to administration and in the sealed state the sealed dose container is devoid of movable internal components that force the medicament out of the dose container, and wherein the dose cartridge first end portion is adapted to slidably receive a syringe in a manner that places the syringe in fluid communication with the internal needle to allow a dose amount of the medicament to be withdrawn by the internal needle and directed into the syringe, wherein the first end of the dose cartridge further comprises an outwardly extending syringe attachment neck with an internal dam that defines a fluid barrier upstream of the dose container, wherein the internal needle resides between the dose container and the neck inside the dose cartridge, and wherein, in position, the syringe disengages the dam to be in fluid communication with the internal needle and the liquid medicament in the dose container.

33. A dose medicament transfer and/or delivery device, comprising:

a dose container comprising an elongate body with a medicament and a compressible longitudinally extending outer wall, wherein the dose container with medicament is adapted to be stored frozen, and wherein the medicament is configured to be in liquid form proximate in time to delivery to a patient;

a cartridge configured to hold the dose container therein; and a plunger in communication with a liquid medicament expulsion system in the cartridge configured to serially expel fixed volumes of liquid medicament from the dose container, wherein the plunger is a manually depressible plunger, wherein the liquid medicament expulsion system comprises a guide rod that engages the plunger, the guide rod having notches, and a pressing mechanism that cooperates with the guide rod and resides outside of and in abutting contact with the dose container outer wall and is configured to slidably advance fixed incremental distances about a length of the dose container in the cartridge to serially expel the fixed volumes of liquid medicament, wherein the plunger is in communication with a roller and a spring, a roller guide and a ratchet held in the cartridge associated with the liquid medicament expulsion system, wherein the spring, roller guide and ratchet cooperate to keep the roller in a forward location in the dose cartridge even when the plunger translates rearward, and wherein the plunger causes the roller to move relative to the roller guide.

34. A device according to claim 33, wherein the dose container elongate body has a planar bottom and at least one planar longitudinally extending wing extending from an outer edge of the body, wherein the expulsion system pressing mechanism comprises a roller with a roller guide that is configured to axially travel from a first end portion of the cartridge toward a second end portion of the cartridge.

35. A device according to claim 33, further comprising a one-way valve in communication with the liquid medicament expulsion system.

36. A dose medicament transfer and/or delivery device, comprising:

a dose container comprising an elongate body with a medicament and a compressible longitudinally extending outer wall, wherein the dose container with medicament is adapted to be stored frozen, and wherein the medicament is configured to be in liquid form proximate in time to delivery to a patient;

a cartridge configured to hold the dose container therein;

a manually depressible plunger in communication with a liquid medicament expulsion system in the cartridge configured to serially expel fixed volumes of liquid medicament from the dose container, wherein the liquid medicament expulsion system comprises a press mechanism that resides outside of and in abutting contact with the dose container outer wall and is configured to slidably advance fixed incremental distances about a length of the dose container in the cartridge to serially expel the fixed volumes of liquid medicament; and an axially translating internal needle held a distance inside the dose cartridge spaced apart from an outer edge portion thereof and configured to travel a fixed path between a retracted home position and an extended position, the device further comprising a patient injection needle directly attached to the dose cartridge and extending outwardly therefrom, wherein the axially translating internal needle is configured to advance to enter the dose container inside the cartridge, and wherein the axially translating internal needle is held inside the cartridge and does not contact the patient during administration of the liquid medicament via the patient injection needle.

37. A device according to claim 36, wherein the axially translating internal needle is configured to be in fluid communication with the dose container to direct liquid medicament to exit therethrough to a channel in the cartridge upstream of the patient injection needle and downstream of the axially translating internal needle to the patient injection needle attached thereto.

38. A device according to claim 37, wherein the axially translating internal needle resides a distance inside the dose cartridge but is proximate the injection needle, and wherein the axially translating internal needle translates independently of the patient injection needle.

39. A device according to claim 36, wherein the axially translating internal needle is configured to be in fluid communication with the opened dose container to direct liquid medicament to exit therethrough to a channel in the cartridge that resides beyond the axially translating internal needle then to an external syringe attached thereto.

40. A device according to any one of claims 1-5, 7-30, 31, 16-23, 33, 34 or 36-35, wherein the liquid medicament comprises a vaccine.

41. A device according to any one of claims 1-5, 7-30, 31, 16-23, 33, 34 or 36-35, wherein the liquid medicament comprises cells.

42. A kit for delivering a liquid medicament, comprising:
a syringe of sterile gas;
a dose container comprising liquid medicament, wherein the dose container is a unitary sealed body with opposing first and second closed ends held in a sealed state enclosing the liquid medicament and in the sealed state the sealed dose container is devoid of movable internal components; and
a cartridge sized and configured to snugly hold the dose container therein, wherein, in use, the syringe of sterile gas is configured to cooperate with the dose container to expel the liquid medicament from the dose container without expelling the sterile gas with the liquid medicament.

43. A method of expelling a liquid medicament from a dose container, comprising:
providing a cartridge holding a sealed dose container having opposing first and second closed end portions with liquid medicament held inside the sealed dose container;
attaching a syringe comprising sterile fluid therein to the cartridge;
piercing a first end of the dose container;
introducing the sterile fluid from the syringe into the first end portion of the dose container; then
pushing only the liquid medicament out of the second end portion of the dose container in response to the introducing step.

44. A method according to claim 43, wherein the sterile fluid is sterile air.

45. A method of delivering a liquid medicament, comprising:
providing a container holding a liquid medicament in a frozen state;
thawing the liquid medicament at a therapy administration site;
heating a needle by inserting the needle into a needle channel of a heater attached to a cartridge that holds the container holding the liquid medicament at the administration site to a sterilization temperature;
piercing the container with the needle after the heating step at the administration site; then
injecting the liquid medicament from the container into the subject after the thawing step.

46. A sealed elongate medicament container comprising a pharmaceutical medicament adapted to be cryogenically frozen then thawed into liquid in the sealed elongate medicament container prior to administration, wherein the sealed elongate medicament container has a unitary compressible body that is tubular with a perimeter defined by substantially parallel long sides merging into first and second opposing closed ends defined by flat sealed edge portions and is configured to be pierced by a needle at an extraction location that is spaced apart from both closed ends, and wherein the container compressible body has sufficient rigidity to maintain its shape with and without liquid medicament held therein,
wherein the sealed elongate medicament container comprises a primary elongate lumen having (i) a substantially constant width throughout the elongate medicament container that holds the medicament and (ii) a secondary elongate lumen that (a) is parallel to and residing over an exterior long side of the sealed container or (b) angularly rises above an outer wall of the tubular container proximate an end portion of the tubular container, wherein the secondary elongate lumen is in fluid isolation from the primary lumen and seals an external surface of the primary lumen prior to extraction of the medicament from the primary lumen to define a sterile extraction surface, and wherein the secondary elongate lumen has a smaller cross-sectional area than the primary elongate lumen.

47. A container according to claim 46, wherein the sealed elongate medicament container has a body, when held in a non-compressed state, that has a substantially planar upper or lower outer surface that extends substantially over an entire length of the medicament container body, and wherein the body has a cross-sectional outer perimeter profile shape with a substantially concave portion merging into the substantially planar outer surface.

48. A container according to claim 46, wherein the long sides of the sealed elongate medicament container comprises first and second longitudinally extending substantially planar wings that extend outwardly off long sides of the elongate medicament container, and wherein the short sides define the opposing ends of the container.

49. A container according to claim 48, further comprising dose data indicia directly on at least one of the wings including (i) a patient specific identifier or a patient name or (ii) a patient specific identifier and a patient name associated with the pharmaceutical medicament in the elongate medicament container.

50. A container according to claim 46, wherein the compressible body of the sealed elongate medicament container is extruded with a wall defining a lumen holding the pharmaceutical medicament therein, wherein the flat sealed edge portions of the compressible body are each formed by opposing sides of the wall thereat being pressed together and sealed, and wherein the sealed elongate medicament container wall has a thickness of about 1/16 inch and an outer diameter of about 3/16 of an inch.

51. A container according to claim 46, further comprising an integral axially extending elongate projection extending above or below a lumen holding the medicament.

52. A container according to claim 46, wherein the sealed elongate medicament container comprises a sterile extraction outer surface residing at the extraction location and the extraction location is closer to one of the closed ends of the container.

53. A container according to claim 52, further comprising a removable protectant member residing over a needle entry port residing on the sterile extraction surface.

54. A container according to claim 52, further comprising a radially outwardly projecting semi-circular member defining a secondary outer channel that resides over the sterile extraction surface and is sealably attached to a wall of a primary lumen, wherein the primary lumen holds the pharmaceutical medicament therein, and wherein the semi-circular member with the secondary outer channel is configured to protect sterility of the sterile extraction surface prior to extraction of the liquid pharmaceutical medicament from the elongate medicament container.

55. A container according to claim 46, wherein the sealed elongate medicament container and the pharmaceutical medicament therein are configured to be held at one or more ultra-low temperatures of below about −40 degrees Celsius.

56. A container according to claim 46, wherein the sealed elongate medicament container and the pharmaceutical medicament therein are held at between about −70 degrees Celsius to about −95 degrees Celsius for a least a portion of a storage period or during shipment or during at least a portion of a storage period and during shipment.

57. A container according to claim 46, wherein the sealed elongate medicament container and the pharmaceutical medicament therein are held at between about −120 degrees Celsius to about −196 degrees Celsius for a least a portion of a storage period or during shipment or during at least a portion of a storage period and during shipment.

58. A container according to claim 46, wherein the sealed elongate medicament container is single-use unit dose medicament container comprising one of the following: polyvinyl chloride (PVC), a Class VI, medical grade TPE tubing polypropylene, polyethylene, polycarbonate and polystyrene, and wherein the medicament container is configured for cryogenic storage.

59. A container according to claim 46, wherein the sealed elongate medicament container is a multi-dose medicament container, and wherein the compressible body comprises one of the following: polyvinyl chloride (PVC), a Class VI, medical grade TPE tubing, polypropylene, polyethylene, polycarbonate and polystyrene, and wherein the multi-dose medicament container is configured for cryogenic storage.

60. A container according to claim 46, wherein the extraction location is on an upper or lower surface of the container proximate one of the closed ends, and wherein the closed ends have substantially the same configuration.

61. A sealed elongate medicament container comprising a pharmaceutical medicament adapted to be cryogenically frozen then thawed into liquid in the sealed elongate medicament container prior to administration, wherein the sealed elongate medicament container has a unitary compressible body that is tubular with a perimeter defined by substantially parallel long sides merging into first and second opposing closed ends defined by flat sealed edge portions and is configured to be pierced by a needle at an extraction location that is spaced apart from both closed ends, and wherein the container compressible body has sufficient rigidity to maintain its shape with and without liquid medicament held therein, wherein the sealed elongate medicament container comprises a sterile extraction outer surface residing at the extraction location and the extraction location is closer to one of the closed ends of the container; and
    a film sealed to the elongate medicament container over the sterile extraction surface.

62. A method of transferring and/or delivering liquid medicament, comprising:
    storing a dose container with a liquid medicament sealably held therein at a temperature sufficient to hold the liquid medicament in a frozen state;
    thawing the frozen liquid medicament in the dose container at a dispensing site while sealed;
    pushing a plunger inward; and
    in response to the pushing step, serially activating or operating a dispensing system associated with a cartridge holding the dose container with the liquid medicament so that the plunger cooperates with a roller guide rod with longitudinally spaced apart notches to automatically cause a pressing member in communication therewith to advance in fixed incremental distances about a length of the dose container and outside of the dose container while the pressing member presses against a longitudinally extending outer wall of the dose container with sufficient force to compress the outer wall of the dose container to cause the liquid medicament to exit the dose container to serially provide a plurality of fixed volume amounts,
    wherein the pressing member comprises a roller, and wherein the serially activating or operating comprises moving the roller unidirectionally axially while pressing against the outer wall of the dose container, the roller having a plurality of serial forward stroke lengths caused by the plunger engaging the roller guide rod at successive spaced apart notched positions that define the exiting fixed volume amounts, wherein the roller rotates about a roll axis that extends outside the dose container in a direction that is substantially orthogonal to a longitudinally extending centerline of the dose container, and wherein the plunger is in communication with the roller and a ratchet held in the cartridge, and wherein the roller and ratchet cooperate to keep the roller in successive forward locations in the dose cartridge even when the plunger translates rearward.

* * * * *

UNITED STATES PATENT AND TRADEMARK OFFICE
CERTIFICATE OF CORRECTION

PATENT NO. : 8,672,879 B2  
APPLICATION NO. : 12/066865  
DATED : March 18, 2014  
INVENTOR(S) : Grant et al.

Page 1 of 1

It is certified that error appears in the above-identified patent and that said Letters Patent is hereby corrected as shown below:

In The Claims:

Column 26, Lines 62-64, Claim 40: Please correct
"any one of claims 1-5, 7-30, 31, 16-23, 33, 34 or 36-35" to read
-- any one of claims 1-5, 7-14, 16, 18-24, 26-37 or 39 --

Column 26, Lines 65-67, Claim 41: Please correct
"any one of claims 1-5, 7-30, 31, 16-23, 33, 34 or 36-35" to read
-- any one of claims 1-5, 7-14, 16, 18-24, 26-37 or 39 --

Signed and Sealed this
Twenty-sixth Day of May, 2015

Michelle K. Lee
*Director of the United States Patent and Trademark Office*

UNITED STATES PATENT AND TRADEMARK OFFICE
CERTIFICATE OF CORRECTION

PATENT NO. : 8,672,879 B2
APPLICATION NO. : 12/066865
DATED : March 18, 2014
INVENTOR(S) : Grant et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 566 days.

Signed and Sealed this
Ninth Day of June, 2015

Michelle K. Lee
*Director of the United States Patent and Trademark Office*